US009297048B2

(12) United States Patent
Balashov et al.

(10) Patent No.: US 9,297,048 B2
(45) Date of Patent: Mar. 29, 2016

(54) **ANTIBIOTIC RESISTANCE PROFILE FOR *NEISSERIA GONORRHOEAE* AND USE OF SAME IN DIAGNOSIS AND TREATMENT OF GONORRHEA**

(75) Inventors: Sergey Balashov, Hamilton, NJ (US); Eli Mordechai, Robbinsville, NJ (US); Martin E. Adelson, East Windsor, NJ (US); Scott E. Gygax, Yardley, PA (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/134,252

(22) Filed: Jun. 2, 2011

(65) Prior Publication Data

US 2012/0071336 A1      Mar. 22, 2012

Related U.S. Application Data

(60) Provisional application No. 61/456,692, filed on Nov. 10, 2010, provisional application No. 61/396,765, filed on Jun. 2, 2010.

(51) Int. Cl.
*C12Q 1/68* (2006.01)

(52) U.S. Cl.
CPC ............ *C12Q 1/689* (2013.01); *C12Q 2600/16* (2013.01)

(58) Field of Classification Search
None
See application file for complete search history.

(56) References Cited

U.S. PATENT DOCUMENTS 6,287,778 B1 *  9/2001  Huang et al. ...................... 506/4

OTHER PUBLICATIONS

Vernel-Pauillac et al., "Rapid detection of a chromosomally mediated penicillin resistance-associated ponA mutation in Neisseria gonorrhoeae using a real-time PCR assay," FEMS Microbiol. Lett., 2006, vol. 255, pp. 66-74.*
Bauwens et al., "Diagnosis of Chlamydia trachomatis urethritis in men by polymerase chain reaction assay of first-catch urine," Journal of Clinical Microbiology, 1993, vol. 31, No. 11, pp. 3013-3016.*
Derrick, J. P. et al. Infection and Immunity 1999; 67(5): 2406-2413.
Hjelmevoll, S. O. et al. Journal of Molecular Diagnositcs 2006; 8(5): 574-581.
Hjelmevoll, S. O. et al. Sexually Transmitted Diseases 2008; 35(5): 517-520.
Defilippis, I. et al. Letters in Applied Microbiology 2007; 45: 426-431.
Goire, N. et al. Diagnostic Microbiology and Infectious Disease 2008; 61: 6-12.
Ito, M. et al. Antimicrobial Agents and Chemotherapy 2005; 49(1): 137-143.
Takahata, S. et al. Antimicrobial Agents and Chemotherapy 2006; 50(11): 3638-3645.
Thulin, S. et al. Antimicrobial Agents and Chemotherapy 2008; 52(2): 753-756.
Ochiai, S. et al. Journal of Clinical Microibiology 2008; 46(5): 1804-1810.
Tanaka, M. et al. International Journal of Antimicrobial Agents 2006; 27: 20-26.
Pnadori, M. et al. Antimicrobial Agents and Chemotherapy 2009; 53(9): 4032-4034.
Ohnishi, M. et al. Antimicrobial Agents and Chemotherapy 2010; 54(3): 1060-1067.
Deguchi, T. et al. Antimicrobial Agents and Chemotherapy 1995; 39(2): 561-563.
Deguchi, T. et al. Antimicrobial Agents and Chemotherapy 1996; 40(4): 1020-1023.
Trees, D. et al. International Journal of Antimicrobial Agents 1999; 12: 325-332.
Sultan, Z. et al. Journal of Clinical Microbiology 2004; 42(2): 591-594.
Vernel-Pauillac, F. et al. Antimicrobial Agents and Chemotherapy 2009; 53(3): 1264-1267.
Tanaka, M. et al. Sex. Transm. Inf. 1998; 74: 59-62.
Shigemura, K. et al. International Journal of Urology 2006; 13: 277-281.
Ropp, P. et al. Antimicrobial Agents and Chemotherapy 2002; 46(3): 769-777.
Shigemura, K. et al. Journal Infect. Chemother. 2005; 11: 226-230.
Kugelman, G. et al. Antimicrobial Agents and Chemotherapy 2009; 53(10): 4211-4216.
Olesky, M. et al. Antimicrobial Agents and Chemotherapy 2002; 46(9): 2811-2820.
Olesky, M. et al. Journal of Bacteriology 2006; 188(7): 2300-2308.
Vernel-Pauillac, F. et al. Antimicrobial Agents and Chemotherapy 2008; 52(9): 3293-3300.
Zarantonelli, L. et al. Antimicrobial Agents and Chemotherapy 1999; 43(10): 2468-2472.

(Continued)

*Primary Examiner* — Young J Kim
(74) *Attorney, Agent, or Firm* — Siu K. Lo

(57) ABSTRACT

The present invention relates to an antibiotic resistance profile for *Neisseria gonorrhoeae* by assessing the presence of mutations (e.g., SNP) in antibiotic resistant genes that confer bacterial resistance against antibiotics such as penicillin, tetracycline, fluoroquinolones, cephalosporin, macrolides and spectinomycin. There is provided a method and a kit for generating an antibiotic resistance profile for *Neisseria gonorrhoeae* by utilizing a multiplex PCR to amplify segments of antibiotic-resistant genes, allele-specific primer extension to detect gene mutation, and detection of such gene mutations with gel electrophoresis, capillary electrophoresis, or DNA microarray. The present method provides useful information to physicians relating the antibiotic susceptibility of *Neisseria gonorrhoeae* against different classes of antibiotics. Relying on this personalized diagnostic tool, physicians can better inform about antibiotic susceptibility and thereby open up medical intervention avenues for treating *Neisseria gonorrhoeae* with antibiotics. There is provided a therapeutic application of the antibiotic resistance profile that has advantages of: (i) providing a more effective regime for gonorrhea treatment; and (ii) halting the evolutionary pressures towards antibiotic resistance in the *Neisseria gonorrhoeae* therapy.

12 Claims, 20 Drawing Sheets

(56) References Cited

OTHER PUBLICATIONS

Dewi, B. E. et al. Sexually Transmitted Diseases 2004; 31(6): 353-359.
Hu, M. et al. Antimicrobial Agents and Chemotherapy 2005; 49(10): 4327-4334.
Ison, C. et al. Sexually Transmitted Diseases 1993; 20(6): 329-333.
Turner, A. et al. Sex. Transm. Inf. 1999; 75: 60-66.
Xia, M. et al. Molecular and Cellular Probes 1995; 9: 327-332.
Elwell, L. P. et al. Antimicrobial Agents and Chemotherapy 1977; 11(3): 528-533.
Dillon, J. R. et al. Molecular and Cellular Probes 1999; 13: 89-92.
Palmar, H. M. et al. Journal of Antimicrobial Chemotherapy 2000; 45: 777-782.
Galimand, M. et al. Antimicrobial Agents and Chemotherapy 2000; 44(5): 1365-1366.

* cited by examiner

ANTIBIOTIC RESISTANCE PROFILE FOR *NEISSERIA GONORRHOEAE* AND USE OF SAME IN DIAGNOSIS AND TREATMENT OF GONORRHEA

CROSS-REFERENCE TO RELATED APPLICATIONS

This application claims the benefit under 35 U.S.C. §119 (e) to U.S. Provisional Application Nos. 61/396,765 filed Jun. 2, 2010 and 61/456,692 filed Nov. 10, 2010, the contents of which are incorporated by reference herein in their entirety.

FIELD OF THE INVENTION

The present invention generally relates to antibiotic resistance in a bacterium that causes a sexually transmitted disease in a human. The present invention specifically provides a profile of antibiotic resistance in *Neisseria gonorrhoeae* by assessing the presence of mutations in antibiotic-resistant genes that confer resistance against antibiotics, such as penicillins (e.g., penicillin), tetracyclines (e.g., tetracycline), fluoroquinolones (e.g., ciprofloxacin), cephalosporin (e.g., cefixime), macrolides (e.g., azithromycin), and aminocyclitols (e.g., spectinomycin). The present method utilizes a multiplex PCR to amplify a segment of an antibiotic-resistant gene in *Neisseria gonorrhoeae*, followed by allele-specific primer extension and detection of same using gel electrophoresis, capillary electrophoresis or DNA microarray. The present profile of antibiotic resistance in *Neisseria gonorrhoeae* provides a physician with diagnostic information specifically tailored to an individual. This personalized diagnostic method surpasses previous diagnostic testing and provides a physician with a useful tool for medical diagnosis and treatment of *Neisseria gonorrhoeae*.

BACKGROUND OF THE INVENTION

Gonorrhea is the second most reported sexually transmitted disease in the United States. According to Centers for Disease Control and Prevention (CDC), an estimated 600,000 new infections occur each year (STD Treatment Guidelines, MMWR 2006). *Neisseria gonorrhoeae* typically infects multiple organs including urethra, cervix, rectum, pharynx, eyes, skin, and joints (Merck Manual) and causes morbidity in humans. *Neisseria gonorrhoeae* often cause painful inflammation and discharge. However, *Neisseria gonorrhoeae* infections can be asymptomatic. Asymptomatic, untreated, and under-treated infections can lead to more severe sequelae such as gonococcal disseminated infections, septic arthritis, and pelvic inflammatory disease (PID). PID can result in preterm labor, chronic pelvic pain, ectopic pregnancies, and sterility in women (CDC, 2003). Antibiotic treatment is the only viable option available today to alleviate the symptoms and cure the *Neisseria gonorrhoeae* infection, yet with declining efficacy.

In 1936, sulfanilamide was first antibiotic introduced to treat *Neisseria gonorrhoeae* in patients. The treatment was ineffective; in large part because of its short-lived efficacy due to rapid emergence of antibiotic resistance, i.e., chromosomal mutations and acquisition of mobile genetic elements from the environment (Workowski et al., 2008).

In 1945, penicillin emerged as a new antibiotic to replace sulfanilamide and since then it gained a wide-spread use in the treatment of gonorrhea. Alexander Fleming discovered penicillin on Sep. 28, 1928, and the penicillin structure was elucidated by Dorothy Crowfoot Hodgkin in 1945. Use of penicillin in the first patient with streptococcal septicemia has made a landmark on Mar. 14, 1942. Thereafter, penicillin has been commercially produced in large quantity. As of 1945, CDC recommended penicillin in the treatment of gonorrhea.

Over time, however, the efficacy of penicillin has notably undergone a progressive decline. *Neisseria gonorrhoeae* has gradually developed penicillin resistance, largely attributed to a series of cumulative chromosomal mutations in several genes (e.g., penA, ponA, penB and mtrR). Each new gene mutation cumulatively increases antibiotic resistance and increases the minimum inhibitory concentration (MIC) for penicillin. In response, CDC recommended an increasing dosage for penicillin (from 50,000 units in 1945 to 4.8 million units by the early 1970s) (Workowski et al., 2008).

Wide-spread and heavy use of penicillin continued to escalate over the years, so did the antibiotic resistance. In 1976, a mobile genetic element (i.e., plasmid) was identified that carries the bla gene (Ashford et al., 1976). The bla gene encodes penicillinase that enables the bacteria to degrade penicillin, leading to an exceedingly high level of penicillin resistance in *Neisseria gonorrhoeae*. In 1985, a new class of chemically modified penicillin (i.e., ceftriaxone), which possess the ability to resist penicillinase, was recommended by the CDC as an alternative treatment regimen for *Neisseria gonorrhoeae*. By 1989, CDC no longer recommended the clinical use of penicillin because of the widespread penicillin resistance.

In 1948, tetracycline is a large antibiotic family that was discovered by Benjamin Minge Duggar. In 1950, Harvard Professor Robert Woodward determined the chemical structure of a tetracycline member (terramycin). The non-β-lactam tetracycline emerged as an alternative antibiotic for gonorrhea. Like penicillin, tetracycline resistance soon developed in *Neisseria gonorrhoeae* after its wide-spread use. The antibiotic resistance mechanism also involves additive chromosomal mutations and plasmid transfer. In 1970-1980's, chromosomal mutations in three genes, mtrR, penB, and rpsJ, caused progressive tetracycline resistance (Hu et al., 2005). In 1983, a highly tetracycline resistant *Neisseria gonorrhoeae* clinical strain was isolated, harboring a plasmid containing the tet(M) gene (CDC, 1985).

In 1993, CDC recommended oral fluoroquinolones (e.g., ciprofloxacin, levofloxacin, and ofloxacin) as well as oral cephalosporin (e.g., cefixime) in *Neisseria gonorrhoeae* treatment. The emergence of quinolone-resistance was observed, again due to chromosomal mutations in the gyrA and parC genes of *Neisseria gonorrhoeae*. By 2000, fluoroquinolone resistant *Neisseria gonorrhoeae* was increasingly noted in patients who became infected in Asia, the Pacific Islands (including Hawaii), and California (San Francisco). In response, CDC no longer recommended fluoroquinolones as a treatment regime in Hawaii. The number of flouroquinolone resistant isolates continued to reach high numbers (>20%). Shortly thereafter, the CDC announced that fluoroquinolones were no longer recommended in other parts of the US.

Presently, CDC recommends only one class of antibiotic (i.e., cephalosporin) for *Neisseria gonorrhoeae* treatment. Ceftriaxone, a member of cephalosporins, is available as an intramuscular injection (125 mg) as the CDC recommended regimen for uncomplicated urogenital and anorectal infection. Cefixime, another member of cephalosporin, is available as an oral regimen (400 mg) as the CDC recommended regimen for gonorrhea treatment. Cephalosporins represent the last resort as the only currently CDC recommended antimicrobial class. It is critical that susceptibility profiles to this remaining class of drug be closely monitored. Unfortunately, recent reports from Japan and Western Pacific Region indicate the appearance of *Neisseria gonorrhoeae* that exhibits a decreased susceptibility to cephalosporins. The underlying mechanism seems to be related to the alterations in penA, mtrR, ponA, and penB (Lee et al., 2010). The emergence and dissemination of such decreased susceptible strains of *Neisseria gonorrhoeae* is of particular concern.

The trend of indiscriminate and over-use of a few antibiotics presents a bleak future. First, heavy use of a few remaining CDC recommended antibiotics hastens evolutionary pressure towards antibiotic resistance. Second, there have been little or no new antibiotics on the horizon invented by pharmaceutical companies indicated for *Neisseria gonorrhoeae* for many years. Accordingly, there remains a great demand for determining an antibiotic resistance profile in *Neisseria gonorrhoeae*, information of such profile is believed to be essential in the antibiotic treatment regime.

BRIEF SUMMARY OF THE INVENTION

The present invention provides a method of generating a profile of antibiotic resistance in *Neisseria gonorrhoeae*. The profile contains information concerning antibiotic resistance against various classes of antibiotics, including, for example, β-lactam, polyketide, fluoroquinolone, cephalosporin, aminocyclitol, and macrolide. In particular, the profile contains information concerning antibiotic resistance against specific antibiotics, including, for example, penicillin, tetracycline, ceftriaxone, ciprofloxacin, spectinomycin, and azithromycin. The method involves detecting using a multiple PCR the presence of gene mutations against at least six (6) genes including penA, penB, rpsJ, gyrA, 16S rRNA and mtrR in *Neisseria gonorrhoeae*. In a preferred embodiment, the multiplex PCR further detects ponA or parC. In a preferred embodiment, the multiplex PCR further detects a gene plasmid such as bla or tet(M).

Preferably, the present method provides a profile of antibiotic resistance in *Neisseria gonorrhoeae* by detecting gene mutations against penicillin, tetracycline, ciprofloxacin, ceftriaxone, spectinomycin and azithromycin. Penicillin is an exemplary antibiotic for β-lactam. Tetracycline is an exemplary antibiotic for polyketide. Ciprofloxain is an exemplary antibiotic for fluoroquinolone. Ceftriaxone (like cefixime) is an exemplary antibiotic for cephalosporin. Spectinomycin is an exemplary for aminocyclitol. Azithromycin is an exemplary for macrolide.

Representative gene mutations for penicillin resistance include penA, ponA, penB, mtrR, or bla. Representative gene mutations for tetracycline resistance include mtrR, tet(M) or rpsJ. Representative gene mutations for fluoroquinolone (e.g., ciprofloxacin) resistance include gyrA, parC or mtrR. Representative gene mutations for cephalosporin resistance include penA. Representative gene mutation for spectinomycin includes 16S rRNA. Representative gene mutation for azithromycin includes mtrR.

The present method provides generating an antibiotic resistance profile for *Neisseria gonorrhoeae*, comprising the steps of a) obtaining a biological sample from a human; b) isolating DNA from said biological sample; c) performing a multiplex PCR against a plurality of genes of penA, penB, rpsJ, gyrA, 16S rRNA and mtrR in *Neisseria gonorrhoeae* to produce respective amplicons of said genes; d) performing a multiplex allele-specific primer extension reaction on said amplicons in step (c) to produce an extended primer; and e) determining the presence of said extended primer, herein the presence of said extended primer is indicative of the presence of a mutation in said genes in *Neisseria gonorrhoeae*, and whereby permits the generation of an antibiotic resistance profile against penicillin, tetracycline, fluoroquinolone, cephalosporin, macrolide and aminocyclitols in *Neisseria gonorrhoeae*.

Preferably, the present method further comprises a multiplex PCR in step (c) to include ponA or parC.

Preferably, the present method further comprises a multiplex PCR in step (c) that includes a gene plasmid selected from the group consisting of bla and tet(M).

Preferably, fluoroquinolone includes ciprofloxacin. Cephalosporin is ceftriaxone or cefixime.

Biological sample includes a vaginal swab, urethral swab, ocular swab or urine.

Isolation of DNA may be performed using guanidine hydrochloride, guanidine thiocyanate, or phenol chloroform.

In preferred embodiments, mutation in penA is selected from the group consisting of G545S, and Asp345A. Mutation in penB is selected from the group consisting of G120D, G120K, A121D, A121S, and A121G. Mutation in rpsJ is V57M. Mutation in gyrA is selected from the group consisting of S91P, S91F, S91Y, D95A, D95G, D95N, and D95Y. Mutation in 16S rRNA is selected from the group consisting of G1064C and C1192U. Mutation in mtrR is selected from the group consisting of G45D, G45S, −35delA, and −10insTT. Mutation in ponA is L421P. Mutation in parC is selected from the group consisting of D86N, S87R, S87N, S88P, E91K, and E91G.

In preferred embodiments, bla gene plasmid is selected from the group consisting of pSJ5, pJD4, pAB6, and pFA7. TetM gene plasmid is pOZ100.

DETAILED DESCRIPTION OF THE INVENTION

Definitions

Figure 1:
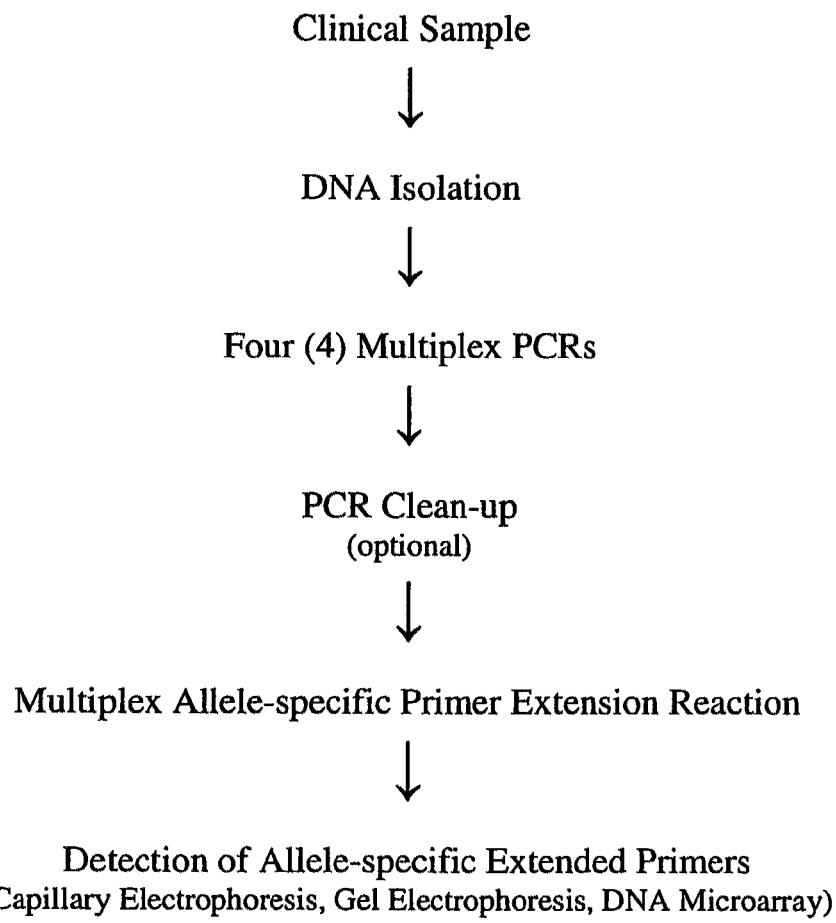
FIG. 1 depicts a flow chart showing the *Neisseria gonorrhoeae* antibiotic resistance panel assay.

Various terms used throughout this specification shall have the definitions set forth herein.

The term "antibiotic" refers to a group of chemical substances, as penicillin or streptomycin, produced by various microorganisms and fungi, having the capacity in dilute solutions to inhibit the growth of or to destroy bacteria and other microorganisms, used chiefly in the treatment of infectious diseases.

The term "antibiotic resistance" refers to a type of drug resistance where a microorganism (e.g., *Neisseria gonorrhoeae* bacterium) has developed the ability to survive exposure to an antibiotic. Evolutionary stress such as exposure to antibiotics selects for the antibiotic resistant trait. A bacterium may carry several resistance genes. Many antibiotic resistance genes reside on plasmids, whose function is to facilitate the transfer of antibiotic resistance genes from one bacterium to another. "Antibiotic resistance" has an opposite meaning as compared to "antibiotic susceptibility", that is, a high antibiotic resistance means a low antibiotic susceptibility and vice versa.

The term "antibiotic resistance profile" refers to a generated profile containing antibiotic resistance information of a specific microorganism (e.g., *Neisseria gonorrhoeae*) against various antibiotics (e.g., penicillin, tetracycline, fluoroquinolone, azithromycin, spectinomycin and cephalosporins).

The term "antibiotic resistance gene" refers to a gene in a bacterium that confers resistance to antibiotics. The mechanisms underlying antibiotic resistance includes, for example, coding an enzyme that destroy antibiotics, coding a surface protein that prevents antibiotics from entering the bacterium, and the like.

The term "mutation" refers to a change the DNA sequence of a bacterium's genome. A mutation can involve, for example, a single nucleotide change, nucleotide insertions or nucleotide deletions. For purposes of this application, many of the chosen gene mutations involve a single nucleotide change (i.e., single nucleotide polymorphism (SNP)).

The term "single nucleotide polymorphism" (SNP) refers to a DNA sequence variation occurring when a single nucleotide—A, T, C, or G—in the genome that differs between members of a paired chromosomes in a microorganism. For example, two sequenced DNA fragments from different microorganisms, AAGCCTA to AAGCTTA, contain a difference in a single nucleotide. In this case we say that there are two alleles: C and T. Almost all common SNPs have only two alleles.

The term "biological sample" refers to tissues or cells derived from a swab such as vaginal swab, uretheral swab, ocular swab; as well as biological fluid such as urine, vaginal secretion and the like.

The term "swab" refers to a stick with a cotton head used in collecting tissue or excretion specimen from an individual.

The term "OneSwab®" refers to a unique, non-invasive, highly stable specimen collection and transport platform proprietary to Medical Diagnostic Laboratories LLC. OneSwab® platform consists of polyester fiber swab, liquid transport medium and polyethylene transport vial.

The term "PCR" or "Polymerase chain reaction" refers to a technique for rapidly producing many copies of a fragment of DNA for diagnostic or research purposes.

The term "multiplex polymerase chain reaction" (multiplex PCR) refers to is a modification of polymerase chain reaction. Multiplex-PCR consists of multiple primer sets within a single PCR mixture to produce amplicons of varying sizes that are specific to different DNA sequences. By targeting multiple genes at once, additional information may be gained from a single test run that otherwise would require several times the reagents and more time to perform.

The term "DNA microarray" refers to a microarray of immobilized single-stranded DNA fragments of a known nucleotide sequence that is used in the identification and sequencing of DNA samples and in the analysis of gene expression.

The term "*Neisseria gonorrhoeae*" (also known as Gonococci (plural), or Gonococcus (singular)) refers to a species of Gram-negative coffee bean-shaped diplococci bacteria responsible for the sexually transmitted disease gonorrhea. *Neisseria gonorrhoeae* was first described by Albert Neisser in 1879.

The term "primer" (also known as "DNA primer" or "oligonucleotide") refers to a short piece of DNA complementary to a given DNA sequence that acts as a point at which replication can proceed, as in a polymerase chain reaction.

The term "allele" refers to any of several forms of a gene, usually arising through mutation that is responsible for hereditary variation. An allele is one of a series of different forms of a genetic locus.

The term "allele-specific primer" refers to a DNA primer designed in a way that the 3' base of oligonucleotide matches to only one of the known gene alleles. Allele-specific primers are used for allele-specific amplification and primer extension.

The term "allele-specific primer extension" refers to an enzymatic reaction of DNA polymerization in which allele-specific primer is extended by DNA polymerase in allele specific manner.

The present inventors discovered a novel method to generate an antibiotic resistance profile in *Neisseria gonorrhoeae*. The present method permits simultaneous determination of antibiotic resistance in *Neisseria gonorrhoeae* against multiple classes of antibiotics. The present method involves the novel use of multiplex PCR followed by multiplex allele-specific primer extension to detect genomic mutations and gene plasmids that confer antibiotic resistance to *Neisseria gonorrhoeae.*

The increasing prevalence of antibiotic resistance in *Neisseria gonorrhoeae* is a cause for health concern. Due to genome plasticity, *Neisseria gonorrhoeae* has developed a resistance to multiple classes of antimicrobial agents decreasing their efficacy for gonorrhea therapy. Emerging antibiotic resistance in *Neisseria gonorrhoeae* calls for new approaches for its assessment and monitoring. The present inventors discovered that an antibiotic resistance profile in *Neisseria gonorrhoeae* can be generated by assessing specific gene mutations that confer resistance against a selected class of antibiotics, specifically include β-lactam, polyketide, fluoroquinolone, cephalosporin, aminocyclitol, and macrolide. Penicillin is an exemplary antibiotic for β-lactam. Tetracycline is an exemplary antibiotic for polyketide. Ciprofloxain is an exemplary antibiotic for fluoroquinolone. Ceftriaxone (like cefixime) is an exemplary antibiotic for cephalosporin. Spectinomycin is an exemplary for aminocyclitol. Azithromycin is an exemplary for macrolide.

Accordingly, the present invention provides an antibiotic resistance profile in *Neisseria gonorrhoeae* that can be generated by assessing specific gene mutations that confer resistance specifically against penicillin, tetracycline, ceftriaxone, ciprofloxacin, spectinomycin, and azithromycin. It is believed that the antibiotic resistance profile generated from the gene mutations against these species is applicable to other members in the antibiotic classes.

The generated antibiotic resistance profile has the advantages of enabling physicians to specifically tailor treatment to an individual infected with *Neisseria gonorrhoeae*. The present method represents a unique personalized diagnostic tool, and yields useful information regarding the antibiotic susceptibility of *Neisseria gonorrhoeae* against a spectrum of antibiotics. The generated antibiotic resistance profile enables a physician to choose a particular antibiotic that the bacterium is susceptible for whereby provides an effective treatment. The present invention thereby provides advantages of a more effective treatment regime. The guidance provided by the antibiotic resistance profile helps to slow down the evolutionary pressures towards antibiotic resistance in the *Neisseria gonorrhoeae* therapy.

Using 40 clinical isolates and a large number (>1,300) of clinical samples, the present inventors selected and studied the genetic profiles of ten (10) genes, which contain a total of thirty (30) gene mutations present in the clinical samples. These include a total of twenty-eight (28) gene mutations and two (2) plasmid genes in *Neisseria gonorrhoeae*. They were specifically chosen for our study. These gene mutations are believed to render antibiotic resistance to the bacterium. Based on the data from our clinical study, the present inventors discovered that a minimum of six (6) gene mutations that is required to generate an antibiotic resistant profile for *Neisseria gonorrhoeae* against six (6) antibiotics. The six (6) gene mutations include penA, penB, rpsJ, gyrA, 16S rRNA and mtrR.

The present invention specifically provides a profile of antibiotic resistance in *Neisseria gonorrhoeae* by assessing the presence of mutations in antibiotic-resistant genes that confer resistance against antibiotics such as β-lactam (e.g., penicillin), polyketide (e.g., tetracycline), cephalosporins (e.g., ceftriaxone or cefixime), macrolides (e.g., azythromycin) and aminocyclitols (e.g., spectinomycin).

There have been numerous reports suggesting a large number of gene mutations and mobile genetic elements that may be associated with a decreased susceptibility of *Neisseria gonorrhoeae* against various antibiotics, such as penicillin, tetracycline, fluoroquinolones (e.g. ciprofloxacin), macrolides (e.g. azithromycin), spectinomycin, and cephalosporins (e.g. cefixime and ceftriaxone). The present inventors selected a total of ten (10) genes in our clinical study. They are penA, penB, bla, ponA, rpsJ, tet(M), gyrA, parC, 16S rRNA, and mtrR. Data from our clinical study reveals that a minimum of six (6) genes (i.e., penA, penB, rpsJ, gyrA, 16S rRNA, and mtrR) and their sequence identification can provide an accurate genetic profile which can be used to predict antibiotic susceptibility to the selected antibiotics. The presence of these mutations is consistently represented in all three (3) groups of the analyzed clinical samples (i.e. the groups consisting of 40, 620, and 1,312 clinical samples). The selected ten (10) genes also provide an accurate genetic profile.

Reduced susceptibility of *Neisseria gonorrhoeae* to penicillin has been suggested to be associated with mutations present in penA, penB, mtrR, ponA, and penC, and the presence of blaTEM-1 gene is found on mobile genetic elements. Upon investigating 40 clinical samples, we identified mutations in 37 penA (95%), 11 penB (28%), 13 mtrR (33%), and 11 ponA (28%) of the clinical samples. The penC mutation has not yet been reported clinically and no blaTEM-1 genes have been identified. Upon investigating an additional 583 clinical samples, mutations in 475 penA (81%), 220 penB (38%), 186 mtrR (32%), and 162 ponA (28%) were identified, as well as 7 samples that possessed the blaTEM-1 (1%) gene (See, Table 11). Further supporting our data, a total of 1,246 clinical samples were investigated in which mutations in 1,046 penA (84%), 440 penB (35%), 399 mtrR (32%), and 355 ponA (28%) were identified, as well as 14 samples that possessed the blaTEM-1 (1%) gene (See, Table 12). Altogether, these clinical studies confirm that our selected six (6) genes represent the dominant and prevalent gene mutations that are accountable for penicillin resistance. Because penA and penB represents the majority gene mutations, the presence of these two (2) gene mutations can provide an accurate genetic profile for penicillin resistance in *Neisseria gonorrhoeae*.

Reduced susceptibility of *Neisseria gonorrhoeae* to tetracycline has been suggested to be associated with mutations present in penB, mtrR, and rpsJ, and the presence of tet(M) gene found on mobile genetic elements. Upon investigating 40 clinical samples, mutations in 11 penB (28%), 13 mtrR (33%), and 24 rpsJ (62%) of the clinical samples were identified, as well as 1 sample that possessed the tet(M) (3%) gene. Similarly, upon investigating an additional 583 clinical samples, mutations in 220 penB (38%), 186 mtrR (32%), and 313 rpsJ (54%) of the clinical samples were identified, as well as 24 samples that possessed the tet(M) (4%) gene (See, Table 11). Further supporting our data, a total of 1,246 clinical samples were investigated in which mutations in 440 penB (35%), 399 mtrR (32%), and 667 rpsJ (54%) were identified, as well as 58 samples that possessed the tet(M) (5%) gene (See, Table 12). Altogether, these clinical studies confirm that rpsJ represents the majority gene mutation associated with tetracycline resistance, the presence of this gene mutation can provide an accurate genetic profile for tetracycline resistance in *Neisseria gonorrhoeae*.

Reduced susceptibility of *Neisseria gonorrhoeae* to ciprofloxacin has been suggested to be associated with mutations present in gyrA, parC, mtrR, and norM. Upon investigating 40 clinical samples, mutations in 3 gyrA (8%), 3 parC (8%), and 13 mtrR (33%) of the clinical samples were identified. The norM mutation has not yet been reported clinically. Similarly, upon investigating an additional 583 clinical samples, mutations in 34 gyrA (6%), 33 parC (6%), and 186 mtrR (32%) of the clinical samples were identified (See, Table 11). Further supporting our data, a total of 1,246 clinical samples were investigated in which mutations in 73 gyrA (6%), 72 parC (6%), and 399 mtrR (32%) of the clinical samples were identified (See, Table 12). Altogether, these clinical studies confirm that gyrA represents the important gene mutation associated with ciprofloxacin resistance, the presence of this gene mutation can provide an accurate genetic profile for ciprofloxacin resistance in *Neisseria gonorrhoeae*.

Reduced susceptibility of *Neisseria gonorrhoeae* to azithromycin has been suggested to be associated with mutations present in mtrR. Upon investigating 40 clinical samples, mutations in 13 mtrR (33%) of the clinical samples were identified. Similarly, upon investigating an additional 583 clinical samples, mutations in 186 mtrR (32%) of the clinical samples were identified (See, Table 11). Further supporting our data, a total of 1,246 clinical samples were investigated in which mutations in 399 mtrR (32%) of the clinical samples were identified (See, Table 12). Altogether, these clinical studies confirm that mtrR represents the majority gene mutation associated with azithromycin resistance, the presence of this gene mutation can provide an accurate genetic profile for tetracycline resistance in *Neisseria gonorrhoeae*.

Reduced susceptibility of *Neisseria gonorrhoeae* to spectinomycin has been suggested to be associated with mutations present in the 16S rRNA. Upon investigating 40 clinical samples, no mutations in the 16S rRNA of the clinical samples were identified. Upon investigating an additional 583 clinical samples, one (1) sample contained mutations in the 16S rRNA (See, Table 11). Further supporting our data, a total of 1,246 clinical samples were investigated in which one (1) sample contained mutations in the 16S rRNA (See, Table 12). The scarcity of 16S rRNA mutation may relay to the fact that this antibiotic is in clinical use only recently. Altogether, these clinical studies confirm that 16S rRNA represents the only reported gene mutation associated with spectinomycin resistance, the presence of this gene mutation can provide an accurate genetic profile for spectinomycin resistance in *Neisseria gonorrhoeae*.

Reduced susceptibility of *Neisseria gonorrhoeae* to cephalosporins (e.g. cefixime and ceftriaxone) has been suggested to be associated with mutations present in penA, penB, mtrR, and ponA genes. In particular, the penA gene associated with reduced susceptibility to the cephalosporins possesses a multitude of nucleotide and amino acid changes thought to be acquired from the penA gene of other *Neisseria* species (i.e., *Neisseria perflava, Neisseria sicca, Neisseria cinerea, Neisseria flavescens, Neisseria polysaccharea,* and *Neisseria meningitides*) by transformation or conjugation and the spontaneous generation of mutations (i.e., G545S) within *Neisseria gonorrhoeae* (Osaka et al., *J. Infect. Chemother.* (2008) 14:195-203). These changes in penA are referred to as mosaic mutations or mosaic penA. Upon investigating 40 clinical samples, mutations in 37 penA (95%), 17 penA-G545S (44%), 11 penB (28%), 13 mtrR (33%), and 11 ponA (28%) of the clinical samples were identified. Similarly, upon investigating an additional 583 clinical samples, mutations in 475 penA (81%), 5 penA-G545S (1%), 220 penB (28%), 186 mtrR (32%), and 162 ponA (28%) were identified (See, Table 11). Further supporting our data, a total of 1,246 clinical samples were investigated in which mutations in 1,046 penA (84%), 7 penA-G545S (1%), 440 penB (35%), 399 mtrR (32%), and 355 ponA (28%) were identified (See, Table 12). The only discrepancy between the three (3) groups of clinical isolates was found with the penA-G545S mutation in which the limited number of samples (40 clinical samples) in the first group found an over representation of the mutation, whereas the two groups (583 and 1,246 clinical samples) with increased numbers of samples were found to be consistent. Altogether, these clinical studies confirm that penA represents the majority gene mutation associated with cephalosporins resistance, the presence of this gene mutation can provide an accurate genetic profile for cephalosporins resistance in *Neisseria gonorrhoeae*.

The literature ponA1-L421P mutation was associated with high-level penicillin resistance. Ropp et al. conducted a detailed study on the contributions of the mutant penA, penB, mtrR, ponA, and penC to penicillin and tetracycline resistance. They reported that the ponA1-L421P mutation does not contribute more than 2-fold increase in MIC resistance above the 6-fold increase contributed from the penA (3-fold), penB and mtrR (3-fold) mutations (Ropp et al., 2002).

The rpsJ-V57M was found to be a good marker for tetracycline resistance for both samples that were both low-resistant (containing rpsJ, penB, and mtrR mutations) and high-resistant (containing the rpsJ-V57M mutation and tet(M) gene) strains (Starnino et al., *FEMS Microbiol. Lett.* (2008) 286:16-23).

The gyrA-S91F represents the primary mutation responsible for fluoroquinolone (e.g. ciprofloxacin) resistance with additional gyrA (D95G, D85A) and parC (S87R, S87N, D86N, E91G) mutations adding incremental increases in MIC (Deguchi et al., 1995; Deguchi et al., 1996; Trees et al., 1999; Sultan et al., 2004). The gyrA-S91F mutation was present in all clinical samples with mutations associated with fluoroquinolone resistance.

Greater than 95% of the non-mosaic penA strains that contain mutations associated with increased resistance to penicillin and cephalosporins contain Asp345a insertion (Ito et al., 2006; Whiley et al., 2007). Emerging non-mosaic penA mutant strains that contain the Asp345a mutation also have additional G542S, P551S/L, and A501V/T mutations that are associated with a greater increased in resistance to the penicillin and cephalosporins and are included in the assay.

The prevalence of the penA-G545S mosaic strains has been reported to be present in the United States in 2008. The five (5) isolates contained mosaic penA, however only three (3) of the five (5) contained the G545S C-terminal mutation and elevated MICs for ceftriaxone and cefixime while the two (2) isolates that did not contain the G545S C-terminal mutation had wild-type MICs for ceftriaxone and cefixime (Pandori et al., 2009). Furthermore, a report that dissected the contribution of the mosaic penA mutations found that the G545S mutation is the primary contributor to the elevated MICs for ceftriaxone and cefixime (Takahata et al., 2006).

In accordance with one embodiment, the present invention provides a method of generating a genetic resistance profile against six (6) antibiotics (e.g., penicillin, tetracycline, ciprofloxacin, cephalosporin, spectinomycin, and azithromycin). In another embodiment, the present invention also provides a method of detecting a total of ten (10) gene mutations so as to provide an accurate genetic profile against the six (6) antibiotics. These ten (10) gene mutations include penA, ponA, penB, mtrR, bla, tet(M), rpsJ, gyrA, parC and 16S rRNA.

Together, the ten (10) gene mutations are shown to be able to reveal the genetic profile against respective antibiotics. They are: (i) penA, ponA, penB, mtrR and bla (for penicillin), (ii) mtrR, tet(M) and rpsJ (for tetracycline), (iii) gyrA, parC, and mtrR (for ciprofloxacin), (iv) penA (for cephalosporin), (v) 16S rRNA (for spectinomycin), and (vi) mtrR (for azithromycin).

In another embodiment, the present invention also provides a minimum number of gene mutations that could accurately reveal the genetic profile against respective antibiotics. Our clinical data show that the detection of a minimal of six (6) gene mutations can provide the generation of a genetic profile associated with antibiotic resistance. These six (6) gene mutations include penA, penB, mtrA, rpsJ, gyrA, and 16S rRNA. The presence of these gene mutations reveals resistance profile with respective to specific antibiotics. They are: (i) penA and penB (for penicillin), (ii) rpsJ (for tetracycline), (iii) gyrA (for ciprofloxacin), (iv) penA (for cephalosporin), (v) 16S rRNA (for spectinomycin), and (vi) mtrR (for azithromycin).

In one embodiment, the present invention is directed to generating a genetic profile against six (6) antibiotics. In another embodiment, the present invention is also directed to generating a genetic profile against five (5), four (4), three (3), two (2) or one (1) antibiotics. Because our clinical data has shown that different gene mutations can provide genetic profile with respect to different antibiotics, one skilled in the art would conveniently determine which gene mutations may be required in order to generate genetic profiles against differing antibiotic classes. For example, a genetic profile against four (4) antibiotics of penicillin, tetracycline, ciprofloxacin, and cephalosporin would require detection of a minimal of gene mutations that would include penA, penB, mtrR, gyrA. A genetic profile against three (3) antibiotics of penicillin, tetracycline and azithromycin would require detection of a minimal of gene mutations that would include penA, penB, rpsJ and mtrR. A genetic profile against two (2) antibiotics of ciprofloxacin, and cephalosporin would require detection of a minimal of gene mutations that would include gyrA and penA. A genetic profile against one (1) antibiotic of spectinomycin would require detection of gene mutation of 16S rRNA. The present application is intended to cover these possible combinations, because they represent mere variants of our invention.

The present inventors use multiplex PCR and allele-specific specific primer extension to delineate genetic profiles of these gene mutations. The generated profile of antibiotic resistance represents a personalized diagnostic assay. The present assay enables a physician to specifically tailor the medical diagnosis and treatment of *Neisseria gonorrhoeae* for a particular individual. There is also disclosed herein a kit required for generating such an antibiotic resistance profile in *Neisseria gonorrhoeae*.

In accordance with one embodiment, the present method provides generating an antibiotic resistance profile for *Neisseria gonorrhoeae* in a human, comprising the steps of a) obtaining a biological sample from a human; b) isolating DNA from said biological sample; c) performing a multiplex PCR against a gene or a gene plasmid to produce an amplicon, wherein said gene or said gene plasmid contains a mutation, wherein said gene consists of penA, penB, rpsJ, gyrA, 16srRNA, and mtrR; d) performing a multiplex allele-specific primer extension reaction on said amplicon in step (c) to produce an extended primer; and e) determining the presence of said extended primer, wherein the presence of said extended primer in step (e) is indicative of the presence of said mutation in said gene in *Neisseria gonorrhoeae*, and wherein permits the generation of an antibiotic resistance profile against penicillin, tetracycline, fluoroquinolone, azithromycin, spectinomycin, and cephalosporin in said human. In another embodiment, the multiplex PCR further targeted against ponA or parC. In yet another embodiment, the multiplex PCR also targeted against a gene plasmid selected from the group consisting of bla and tet(M).

The present invention provides a method of determining the presence of mutations in genes that offer penicillin resistance in *Neisseria gonorrhoeae*. The selected penicillin resistant genes or gene plasmids include penA, ponA, penB, mtrR, or bla. The gene mutations include Asp345A of penA gene; L421P of ponA gene; G120D, G120K, A121D, A121S and A121G of penB gene; and G45D, G45S, −35delA and −10insTT of mtrR gene. The gene plasmid includes bla.

The present invention also provides a method of determining the presence of gene mutations for tetracycline resistance. The selected tetracycline resistant genes include mtrR, tet (M), or rpsJ. The gene mutations include G45D, G45S, −35delA and −10insTT of mtrR gene; and V57M of rpsJ gene. The gene plasmid includes tet(M).

The present invention also provides a method of determining the presence of mutations in genes that provide antibiotic resistance against fluoroquinolone such as ciprofloxacin. The selected fluoroquinolone resistant genes include gyrA, parC or mtrR. The gene mutations include S91P, D95A, D95G, D95N, S91Y, S91F and D95Y of gyrA gene; and D86N, S87R, S87N, S88P, E91K and E91G of parC gene; and G45D, G45S, −35delA and −10insTT of mtrR gene The present invention also provides a method of determining the presence of gene mutations for azithromycin resistance. The selected azithromycin resistant gene includes mtrR. The gene mutations include G45D, G45S, −35delA and −10insTT of mtrR gene.

The present invention also provides a method of determining the presence of gene mutations for spectinomycin resistance. The selected spectinomycin resistant gene includes 16S rRNA gene. The gene mutations include G1064C and C1192U of 16S rRNA gene.

The present invention also provides a method of determining the presence of gene mutations for cephalosporin resistance. The selected cephalosporin resistant gene includes penA gene. The gene mutation includes G545S of penA gene.

In accordance with one embodiment, biological sample includes, but not limited to, a vaginal swab, urethral swab, ocular swab, urine and the like.

In order to evaluate a plurality of gene mutations simultaneously, the present method provides a multiplex PCR designed to amplify DNA segments containing the gene mutations of particular genes. After a biological sample is collected from a human subject, DNA is isolated using standard methods that are known to one skilled in the art. Exemplary DNA isolation procedures include the use of guanidine hydrochloride, guanidine thiocyanate, phenol chloroform and the like.

Detection of gene mutations in a specific gene is known in the art. There are many methodologies that allow the detection of gene mutations. Exemplary embodiments of the gene mutation detection method include, for example, (i) direct sequencing (ii) PCR followed by sequencing; (iii) PCR followed by pyrosequencing and the like.

In accordance with one embodiment of the present invention, gene mutation is detected by direct sequencing. A variety of automated sequencing procedures can be utilized ((1995) *Biotechniques* 19:448), including sequencing by mass spectrometry (See, e.g., PCT International Publication No. WO94/16101; Cohen et al., *Adv. Chromatogr.* 36:127-162 (1996); and Griffin et al., *Appl. Biochem. Biotechnol.* 38:147-159 (1993)). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

In accordance with another embodiment of the present invention, gene mutation is detected by PCR followed by sequencing. For example, a PCR is performed to produce an amplicon containing a putative gene mutation. The putative gene mutation is subsequently detected by sequencing the amplicon produced by the PCR. To perform sequencing, one skilled in the art may employ a sequencing primer in conjunction with a sequencing instrument (e.g., ABI 3130 Genetic Analyzer).

According to non-limiting example embodiments, the PCR may be a real-time PCR. Real-time PCR is preformed with primers that utilize the 5' exonuclease activity of thermostable polymerases such as Taq to cleave dual-labeled probes present in the amplification reaction (See, e.g., Wittwer, C. et al. *Biotechniques* 22:130-138, 1997). While complementary to the PCR product, the primer probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-floruescein moiety and the like. Exemplary quenchers include Black Hole Quencher 1 moiety and the like.

In another embodiment, real-time PCR methods may include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996).

In another embodiment, real-time PCR methods may also include the use of one or more hybridization probes, which may also be determined by those skilled in the art, in view of this disclosure. Exemplary probes such as the HEX channel and/or FAM channel probes, as understood by one skilled in the art.

In accordance with one embodiment with the present invention, gene mutation may also be detected by PCR followed by pyrosequencing. Pyrosequencing generally involves a cascade of four enzymatic reactions that permit the indirect luciferase-based detection of the pyrophosphate released when DNA polymerase incorporates a dNTP into a template-directed growing oligonucleotide. Each dNTP is added individually and sequentially to the same reaction mixture, and subjected to the four enzymatic reactions. Light is emitted only when a dNTP is incorporated, thus signaling which dNTP in incorporated. Unincorporated dNTPs are degraded by apyrase prior to the addition of the next dNTP. The method can detect heterozygous individuals in addition to heterozygotes. Pyrosequencing uses single stranded template, typically generated by PCR amplification of the target sequence. One of the two amplification primers is biotinylated thereby enabling streptavidin capture of the amplified duplex target. Streptavidin-coated beads are useful for this step. The captured duplex is denatured by alkaline treatment, thereby releasing the non-biotinylated strand.

Provided herein also includes a method involving a multiplex PCR followed by a multiplex allele-specific primer extension. This approach represents a non-limiting exemplary method to detect gene mutations.

Multiplex PCR allows an investigator to assay two or more different gene targets in a single reaction through the use of multiple primers and probes, each specific for its own target and each comprising a fluorescent moiety that emits at a unique wavelength. Multiplex PCR is possible with Taq-Man® probes, Molecular Beacons, and Scorpions, as recognized by one skilled in the art. Due to its non-specific binding nature, SYBR® Green may not be amenable to multiplex PCR.

Multiplex PCR functions to generate a gene fragment (i.e., amplicon) containing a gene mutation. The design of specific primer sets to amplify a gene to generate such an amplicon is generally known. One skilled in the art would conveniently design primers to amplify a gene segment hosting the gene mutation. The location and length of primers can vary so long as it can achieve the function of preparing an amplicon sufficient in length for the allele-specific primer extension reaction to detect gene mutation. Preferably, the primer length may vary from 18-30 basepairs. The specific primer sets used in amplifying the ten (10) genes are listed in Table 2.

To detect the presence of gene mutation present on the amplicons, we used allele-specific primer extension method.

Allele-specific primer extension method is a molecular assay used for assessing gene mutations or single nucleotide polymorphisms (SNPs). Allele-specific primer extension method is known in the art after its development in the 1980s. To perform an allele-specific primer extension reaction, specific primer is designed in a way that variable base or mutation is the base located at the 3' end the primer sequence. Detection of either normal or mutant allele requires a separate extension primer. Extension of the allele-specific primer depends on perfect complementarity of the base at its 3' end. Specificity of the allele-specific primer extension reaction is determined by the intrinsic property of the DNA polymerase. The DNA polymerase only initiates DNA synthesis when allele-specific primer perfectly hybridizes to the single stranded DNA template at its 3' end. The perfect hybridization thereby provides free 3' end hydrohyl group for the formation of a phosphodiester bridge between 3'-hydroxyl group of deoxyribose sugar residue of last nucleotide of the primer and 5'-hydroxyl group of deoxyribose sugar residue of incoming nucleotide. On the other hand, if the base at the 3' end of the allele-specific primer does not perfectly hybridize to the single stranded DNA template, there is no primer extension reaction by the DNA polymerase.

A variety of methodologies may be used for detection of the allele-specific primer extension reaction products. Such methods may include gel electrophoresis, capillary electrophoresis, mass spectrometry, DNA micro arrays, and the like. For instance, Singer-Sam et al. described allele-specific primer extension reaction analysis by gel electrophoresis; Vallone et al. described allele-specific primer extension assay based on capillary electrophoresis; Pastinen et al. described a system for genotyping by allele-specific primer extension on micro-arrays; O'Meara et al. described SNP typing by apyrase-mediated allele-specific primer extension on DNA micro-array; and Sauer et al. published a review on SNP analysis using allele-specific primer extension assay by mass spectrometry.

It is known that labeling products of allele-specific primer extension reaction with modified nitrogeneous bases may facilitate the detection of the allele-specific primer extension reaction products. To this end, biotin-labeled dNTPs are frequently used for such purpose. Labeling of DNA oligonucleotides with biotin and subsequent streptavidin-phycoerythrin coupling and colorimetric detection is also used in the detection of allele-specific primer extension reaction products. In one embodiment, DNA polymerase extends the hybridized primer by incorporation of labeled deoxynucleotides (dNTPs). In another embodiment, DNA polymerase extends the hybridized primer by incorporation of labeled dideoxynucleotides (ddNTPs).

Multiplex allele-specific primer extension reaction may be used in this invention. Multiplex allele-specific primer extension requires amplification of multiple gene mutations using a plurality of allele-specific primers. The design of multiplex allele-specific primers is known in the art insofar as there is no interference of these primers in the multiplex primer extension reaction. Multiplex allele-specific primer extension reaction may be performed using arrayed primer extension technology that is arrayed on a glass slide. Such customizable high throughput multiplex platforms are known in the art.

Also provided herein is a detection kit typically containing one or more primer sets (specific for multiplex PCR to amplify DNA fragments containing specific gene mutations) in accordance to the present invention of generating a genetic profile against different antibiotics. Multiple pairs of allele-specific extension primers may also be included in the kit to simultaneously determine the presence of gene mutations. Instruction for performing the detection assay also included in the kit.

The invention can be understood more fully by reference to the following illustrative examples, which are intended to exemplify non-limiting embodiments of the invention.

EXPERIMENTAL STUDIES

The invention can be understood more fully by reference to the following illustrative examples, which are intended to exemplify non-limiting embodiments of the invention.

Example 1

Selection of Genetic Markers for Antibiotic Resistant Profile in Neisseria gonorrhoeae A) Antibiotic Resistance Panel In this study, we examined the antibiotic resistance profile of Neisseria gonorrhoeae against a panel of antibiotics. To this end, we chose six (6) antibiotics that are relevant in the evolution of antibiotic resistance developed during the years for Neisseria gonorrhoeae. These antibiotics included: (1) penicillin, (2) tetracycline, (3) floroquinolones (including ciprofloxacin, levofloxacin, and ofloxacin), (4) cephalosporin, (5) azithromycin, and (6) spectinomycin.

B) Genetic Markers for Antibiotic Resistant Panel in Neisseria gonorrhoeae

Table 1 summarizes the mutations and genetic markers included in the antibiotic resistant panel for Neisseria gonorrhoeae.

TABLE 1

| Phenotypes | Genes | Mutations/Genetic Marker |
|---|---|---|
| Neisseria gonorrhoeae speciation | porA | Neisseria gonorrhoeae marker |
| Penicillin, cephalosporin resistance | penA | Asp345A, G545S |
| Ciprofloxacin resistance | gyrA | S91P, D95A, D95G, D95N S91Y, S91F, D95Y |
| Ciprofloxacin resistance | parC | D86N, S87R, S87N, S88P, E91K, E91G |
| Penicillin resistance | ponA | L421P |
| Penicillin resistance | penB | G120D, G120K, A121D, A121S, A121G |
| Penicillin, ciprofloxacin, tetracycline, azithromycin resistance | mtrR | G45D, G45S, −35delA, −10insTT |
| Tetracycline resistance | tet(M) | Plasmid tet gene on plasmid pOZ100 |
| Tetracycline resistance | rpsJ | V57M |
| Penicillin resistance | bla | Plasmid bla gene (b-lactamase) on plasmids pSJ5, pJD4, pAB6, and pFA7. |
| Spectinomycin resistance | 16s rRNA | G1064C, C1192U |

Note that porA gene is selected to indicate the speciation for Neisseria gonorrhoeae. That is, the presence of porA gene indicates the presence of Neisseria gonorrhoeae (and not other species such as Neisseria meningitides, Neisseria mucosa, Neisseria cinerea, Neisseria sicca, Neisseria perflava, Neisseria flavescens, Neisseria lactamica).

As shown in Table 1, the genes (and their respective mutations/genetic markers) for penicillin resistance include ponA (L421P), penB (G120D, G120K, A121D, A121S and A121G), mtrR (G45D, G45S, −35delA and −10insTT), penA (Asp345A) and bla (Plasmid bla gene (b-lactamase) on plasmids pSJ5, pJD4, pAB6, and pFA7).

The genes (and their respective mutations/genetic markers) for tetracycline resistance include mtrR (G45D, G45S, −35delA and −10insTT), tet(M) (Plasmid tet gene on plasmid pOZ100) and rpsJ (V57M).

The genes (and their respective mutations/genetic markers) for fluoroquinolone resistance include gyrA (S91P, D95A, D95G, D95N S91Y, S91F and D95Y), parC (D86N, S87R, S87N, S88P, E91K and E91G) and mtrR (G45D, G45S, −35delA and −10insTT).

The gene (and its respective mutations/genetic markers) for cephalosporin resistance is penA (G545S).

The gene (and its respective mutations/genetic markers) for azithromycin resistance is mtrR (G45D, G45S, −35delA and −10insTT).

The gene (and its respective mutations/genetic markers) for spectinomycin resistance is 16S rRNA (G1064C and C1192U).

Example 2

Development of Antibiotic Resistance Assay for *Neisseria gonorrhoeae*

FIG. 1 is a flow chart summarizing the overall steps for our antibiotic resistance assay. Note that the assay involves multiplex PCRs, followed by allele-specific primer extensions and detection means (e.g., capillary electrophoresis, gel electrophoresis or DNA micro array).

Primer Designs—Multiplex PCR

DNA was isolated from either cells obtained from ATCC or clinical samples (e.g., cervical swab) using standard protocols (i.e., guanidine thiocyanate extraction). Multiplex PCR primers were designed using Beacon Designer software v5.0 (Premier Biosoft, CA). The choice of primers was determined using several parameters including primer length, primer melting temperature, primer annealing temperature and GC content. These primers were selected to avoid hairpin and primer-dimer formation (i.e., avoid possible non-specific hybridization). In our assay, we performed four (4) multiplex PCR. This permits a rapid amplification of genes via multiplex PCRs that lack interference.

In the first multiplex PCR, three (3) sets of primer pairs were used against penA (G545S), ponA (L421P) and penB (G120D, G120K, A121D, A121S and A121G).

In the second multiplex PCR, three (3) sets of primers were used against porA (selected to indicate the speciation for *Neisseria gonorrhoeae*), penA (Asp345A) and rpsJ (V57M).

In the third multiplex PCR, three (3) sets of primers were used against gyrA (S91P, D95A, D95G, D95N S91Y, S91F and D95Y), parC (D86N, S87R, S87N, S88P, E91K and E91G) and 16S rRNA (G1064C and C1192U).

In the fourth multiplex PCR, three (3) sets of primers were used against mtrR (G45D, G45S, −35delA and −10insTT), bla (Plasmid bla gene (b-lactamase) on plasmids pSJ5, pJD4, pAB6, and pFA7) and tet(M) (Plasmid tet gene on plasmid pOZ100).

Table 2 summarizes the four (4) multiplex PCRs (described above) as well as the primer sequences designed for the multiplex PCRs in order to obtain specific PCR products (amplicons) as determined by the PCR fragment sizes (bp).

TABLE 2

| PCR | Genes | Mutations/ Genetic Markers | Forward (F) & Reverse (R) Primers | Primer Nucleotide Sequences | PCR Fragment size by |
|---|---|---|---|---|---|
| PCR 1 | penA | G545S | penA-F | CCGTGTGATTGTGGCGGTAACC (SEQ ID NO: 1) | 116 |
| | | | penA-R1 | TGCCCAAGATGTTCAGGCTGC (SEQ ID NO: 2) | |
| | ponA | L421P | ponA-F | GAGCGGTCGATAATGAGAAAATGG (SEQ ID NO: 3) | 133 |
| | | | ponA-R | GCATCCAGCGAAACCAAAGC (SEQ ID NO: 4) | |
| | penB | G120D, G120K, A121D, A121S, A121G | penB-F2 | CAACAAACAATCCTTCGTCGGCTTG (SEQ ID NO: 5) | 202 |
| | | | penB-R2 | GGCAAATTCGGGAGAATCGTAGCG (SEQ ID NO: 6) | |
| PCR 2 | porA | porA | porA-F | CCGTGCGTTACGATTCCCCC (SEQ ID NO: 7) | 136 |
| | | | porA-R | ACAGCCGGAACTGGTTTCATCTG (SEQ ID NO: 8) | |
| | penA | Asp345A | penA-Asp345A-F | TTCGGCAATCAAACCGTTCGTG (SEQ ID NO: 9) | 179 |
| | | | penA-Asp345A-R | TGCTTGTGCCGACGTTGGAC (SEQ ID NO:10) | |
| | rpsJ | V57M | rpsJ-F | GCGTTTCAACATTTTGCGTTCTCC (SEQ ID NO: 11) | 116 |
| | | | rpsJ-R | CATCGGTAGTTTTATCGGTCCAATCC (SEQ ID NO: 12) | |
| PCR 3 | gyrA | S91P, D95A, D95G, D95N | gyrA-R | AAAATAACTGGAATGCCGCCTAC (SEQ ID NO: 13) | 161 |
| | | | gyrA-F | GAAGTTGCCCTGTCCGTCTATC (SEQ ID NO: 14) | |

TABLE 2-continued

| PCR | Genes | Mutations/ Genetic Markers | Forward (F) & Reverse (R) Primers | Primer Nucleotide Sequences | PCR Fragment size by |
|---|---|---|---|---|---|
| | parC | S91Y, S91F, D95Y D86N, S87R, S87N, S88P, E91K, E91G | parC-F<br>parC-R1 | CGTGGTCGGCGAGATTTTGG (SEQ ID NO: 15)<br>CGAACCGAAGTTGCCGATGC (SEQ ID NO: 16) | 130 |
| | 16S_rRNA | G1064C, C1192U | 16s_rRNA-F1<br>16s_rRNA-R1 | AGCCGTAACACAGGTGCTGC (SEQ ID NO: 17)<br>GACCATTGTATGACGTGTGAAGCC (SEQ ID NO: 18) | 209 |
| PCR 4 | mtrR | G45D, G45S, -35delA, -10insTT | mtrR-F<br>mtrR-R | GGGTTTCATTATACATACACGATTGC (SEQ ID NO: 19)<br>GATGTCGTCGCAGATACGTTGG (SEQ ID NO: 20) | 296 |
| | Bla | bla | bla-F5<br>bla-R5 | ATAGACAGATCGCTGAGATAGGTGC (SEQ ID NO: 21)<br>AAAAGCGGTTAGAGCGGCTATTG (SEQ ID NO: 22) | 265 |
| | tet(M) | tet(M) | tetM-3' external-F<br>tetM_pl-R2 | CCAGCCCCGTCGTCCAAATAGTC (SEQ ID NO: 23)<br>GCATCAATCATTTGCTCATGTGGC (SEQ ID NO: 24) | 190 |

Figure 2:
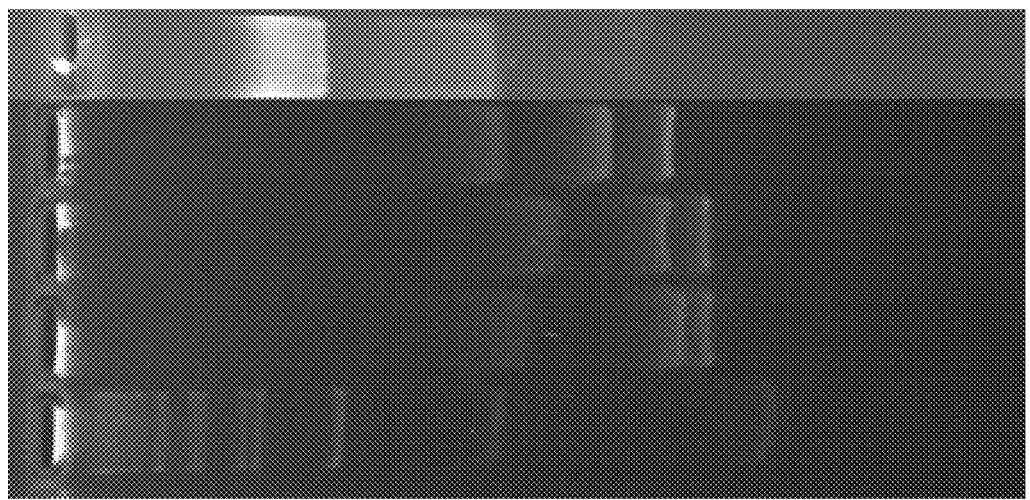
FIG. 2 depicts an agarose gel containing amplicons from four (4) *Neisseria gonorrhoeae* antibiotic resistance multiplex polymerase chain reactions (PCR). Lane 1 contains a 100 bp DNA size standard (USB/Affymetrix, CA). Lane 2 contains amplicons from multiplex PCR 1 (amplicon sizes of 116 bp, 133 bp and 202 bp). Lane 3 contains amplicons from multiplex PCR 2 (amplicon sizes of 116 bp, 136 bp and 179 bp). Lane 4 contains amplicons from multiplex PCR 3 (amplicon sizes of 130 bp, 161 bp and 209 bp). Lane 5 contains amplicons from multiplex PCR 4 (amplicon sizes of 190 bp, 265 bp and 296 bp).
Figure 3:
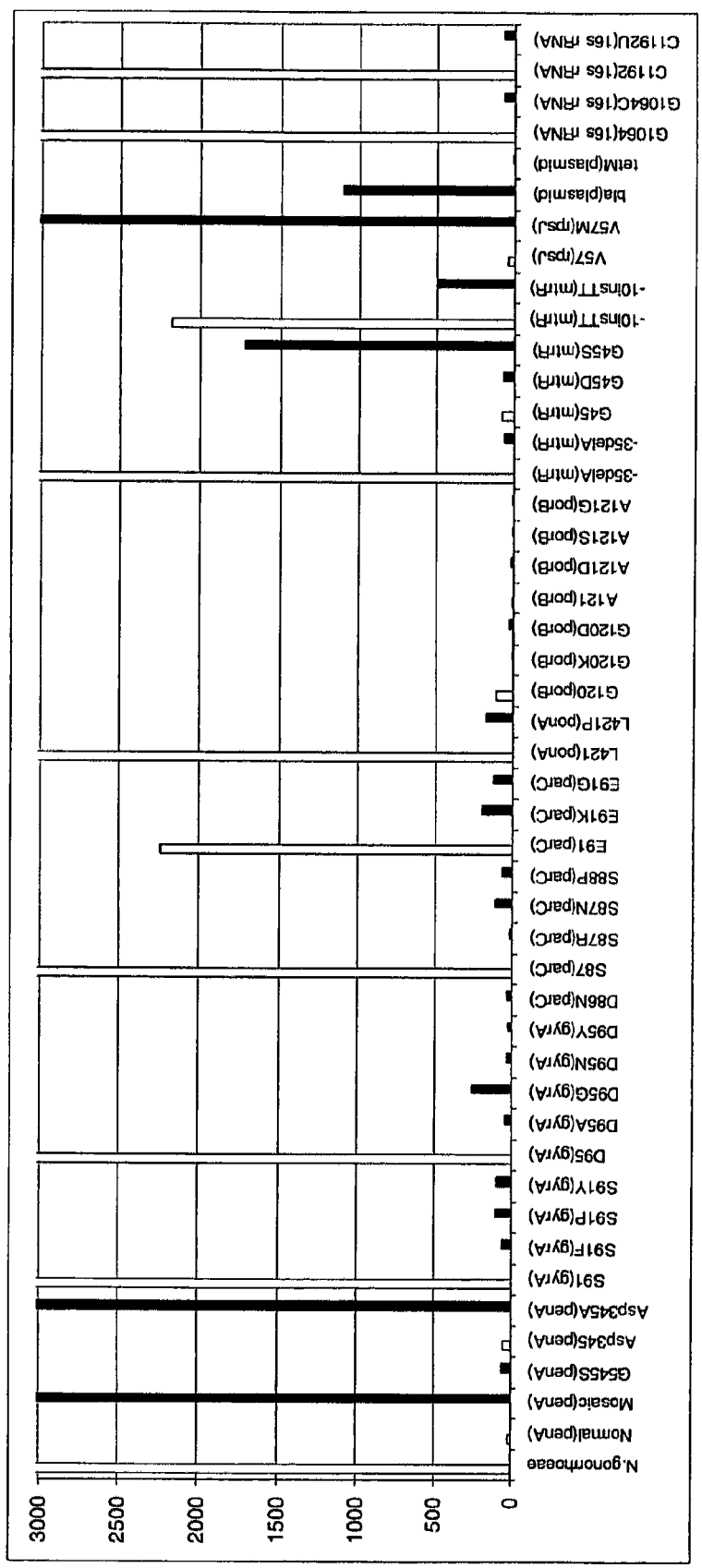
FIG. 3 depicts the profile of antibiotic resistance in *Neisseria gonorrhoeae* strain ATCC 49981. Normal alleles are shown by white bars. Mutant alleles, confirming resistance, are shown by black bars.
Figure 4:
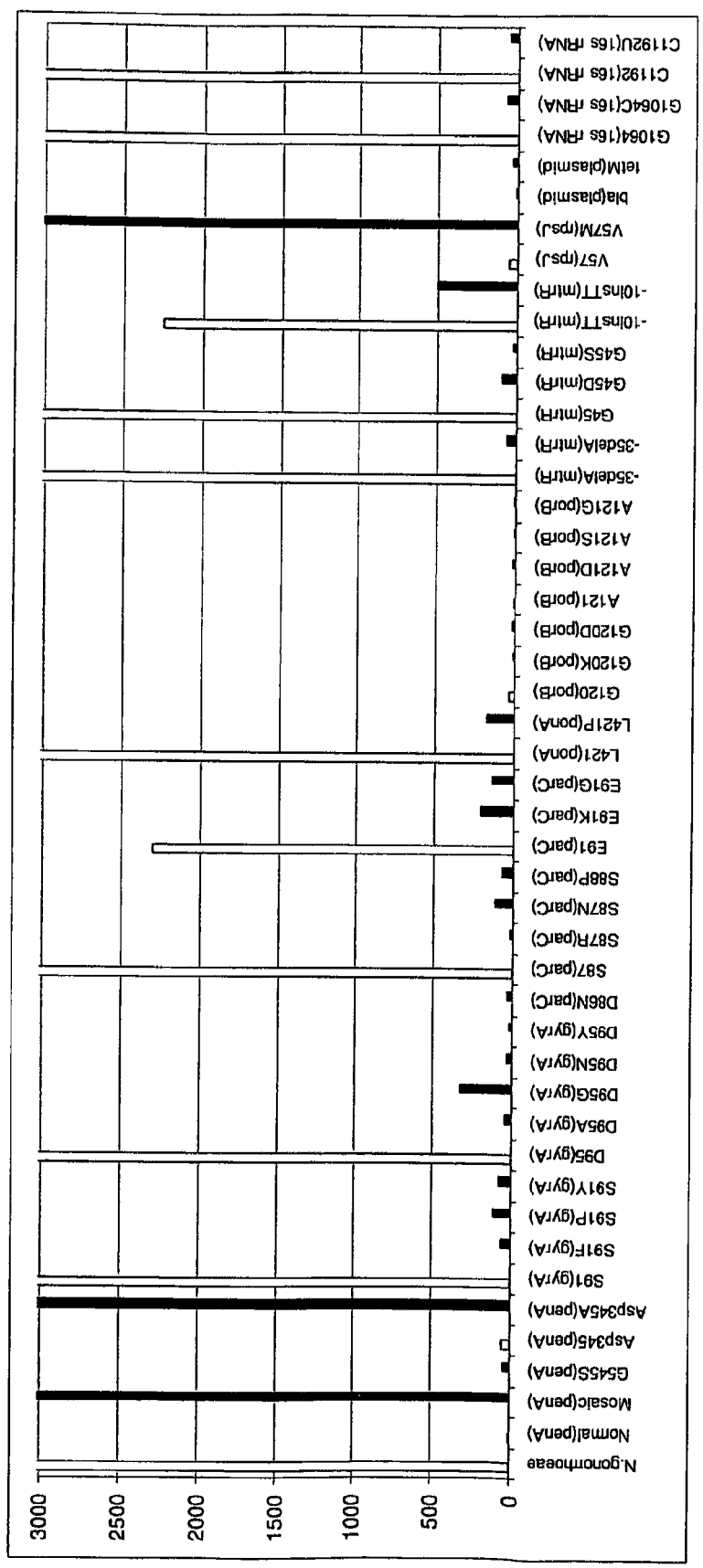
FIG. 4 depicts the profile of antibiotic resistance in *Neisseria gonorrhoeae* strain ATCC 49226. Normal alleles are shown by white bars. Mutant alleles, confirming resistance, are shown by black bars.

FIG. 2 summarizes the results from the four (4) multiplex PCRs. Lane 1 represents the standards. Lanes 2-5 represent the amplicon products from the four (4) multiplex PCRs respectively. This result indicates that the four (4) multiplex PCRs worked properly to amplify various antibiotic resistance genes.

Example 3

PCR Clean-Up

It is optional to clean-up the amplicons generated after the four (4) multiplex PCRs, prior to the multiplex allele-specific primer extension reaction. In this example, we performed the optional step.

After the multiplex PCR, Exo-SAP was added directly to the PCR products. The reaction mixture was incubated at 37° C. for 15 minutes (See, FIG. 1). Exo-SAP reagent was designed for simple, quick PCR clean-up for downstream applications, such as Single Nucleotide Polymorphism (SNP) analysis. When PCR amplification was complete, any unconsumed dNTPs and primers remaining in the PCR product mixture may interfere with these methods. Exo-SAP aided to remove PCR contaminants. After Exo-SAP treatment, excess Exo-SAP was inactivated by heating to a temperature of 80° C. for 15 minutes.

Example 4

Multiplex Allele-Specific Primer Extension—Primer Design

Using primers listed in Example 2, multiplex PCR were performed to simultaneously PCR amplify multiple regions (i.e., 3 sites) of several genes. In this example, we optimized our assay for multiplex detection of SNPs (or mutations/genetic markers) at various positions for respective genes (details of the 10 genes and 30 mutations/genetic markers are provided in Table 1).

To achieve this goal, we employed allele-specific primer extension for multiplex detection of SNPs.

A) Criteria for Primer Design

Allele-specific primers were designed using BatchPrimer3 v1.0 web based software. The 3' terminal base of the allele-specific primer sequences was designed to match either the normal or the mutant base in the *Neisseria gonorrhoeae* chromosomal allele sequence. Annealing of an allele-specific primer sequence to its matched *Neisseria gonorrhoeae* chromosomal allele sequence permits the primer extension reaction to occur. The choice of primers included using several parameters, such as complementary to the mutation regions. These primers were selected to avoid hairpin and primer-dimer formation (i.e., avoid possible non-specific hybridization) as well as an annealing temperature of approximately 60° C.

Once allele-specific primers were selected, we modified the 5' end of the primers by adding nucleotide sequences complimentary to nucleotide sequences via covalently linked to flow cytometric microspheres. Allele-specific extended primers containing the 5' modification were captured by their complimentary nucleotide sequences covalently linked to the flow cytometric microspheres, thus facilitating sorting and detection of the allele-specific extended primers.

B) Selected Primers for Allele-Specific Primer Extension

We chose a panel of antibiotic resistance genes to generate an antibiotic resistance profile. This includes penicillin, tetracycline, ciprofloxacin, cephalosporin, azithromycin and spectinomycin. The present inventors believe that this selected panel of antibiotics can provide a broad and adequate spectrum regarding antibiotic resistance in *Neisseria gonorrhoeae*.

Table 3 summarizes the penicillin resistance genes, the respective mutations/genetic markers, as well as the nucleotide sequences for the selected primers used in our allele-specific primer extension reaction.

TABLE 3

| Penicillin-resistance Genes | Mutations/ Genetic Markers | Allele-Specific Primer Extension Primers |
|---|---|---|
| penA | Asp345A | CTTTTCAATTACTTCAAATCTTCAAAGAGGGGTAAACA TGGGTATCGT (SEQ ID NO: 25) |
| | | TCATTCATATACATACCAATTCATAAGAGGGTAAAC ATGGGTATCGC (SEQ ID NO: 26) |
| ponA | L421P | TCAACAATCTTTTACAATCAAATCGGTGGTTCAAGAGC CGTTGCC (SEQ ID NO: 27) |
| penB | G120D | ATTATTCACTTCAAACTAATCTACCAGCCCCCTGAAAA ACACCGA (SEQ ID NO: 28) |
| | G120K | TACATTACCAATAATCTTCAAATCCAGCCCCCTGAAAA ACACCA (SEQ ID NO: 29) |
| | A121D | CTACATATTCAAATTACTACTTACGGATTCCCAAGCAT TGACGTTGT (SEQ ID NO: 30) |
| | A121S | AATCTAACAAACTCATCTAAATACGGATTCCCAAGCAT TGACGTTGCT (SEQ ID NO: 31) |
| | A121G | CTATCTTCATATTTCACTATAAACGGATTCCCAAGCAT TGACGTTGCC (SEQ ID NO: 32) |
| mtrR | G45D | TCAACTAACTAATCATCTATCAATTTTGAAATGCCAAT AGAGCGCGT (SEQ ID NO: 33) |
| | G45S | AATCAATCTTCATTCAAATCATCATTTGAAATGCCAAT AGAGCGCGCT (SEQ ID NO: 34) |
| | -35delA | TAATCTTCTATATCAACATCTTACTTATACATACACGA TTGCACGGATAAAAA (SEQ ID NO: 35) |
| | -10insTT | CTTTTACAATACTTCAATACAATCGGTTTGACGAGGGC GGATTATAAAAAAG (SEQ ID NO: 36) |
| Bla | pSJ5 pJD4 pAB6 pFA7 | TCATAATCTCAACAATCTTTCTTTGCTGAGATAGGTGC CTCACTGATTAAGC (SEQ ID NO: 37) |

Table 4 summarizes the tetracycline resistance genes, the respective mutations/genetic markers, as well as the nucleotide sequences for the selected primers used in our allele-specific primer extension reaction.

TABLE 4

| Tetracycline-resistance Genes | Mutations/ Genetic Markers | Allele-Specific Primer Extension Primers |
|---|---|---|
| mtrR | G45D | TCAACTAACTAATCATCTATCAATTTTGAAATGCCAAT AGAGCGCGT (SEQ ID NO: 33) |
| | G45S | AATCAATCTTCATTCAAATCATCATTTGAAATGCCAAT AGAGCGCGCT (SEQ ID NO: 34) |
| | -35delA | TAATCTTCTATATCAACATCTTACTTATACATACACGA TTGCACGGATAAAAA (SEQ ID NO: 35) |
| | -10insTT | CTTTTACAATACTTCAATACAATCGGTTTGACGAGGGC GGATTATAAAAAAG (SEQ ID NO: 36) |
| tet(M) | pOZ100 | TCATTTACCAATCTTTCTTTATACCCCGTCGTCCAAATA GTCGGATAG (SEQ ID NO: 38) |
| rpsJ | V57M | CAATATCATCATCTITATCATTACAACATTITGCGTTCT CCGCACA (SEQ ID NO: 39) |

Table 5 summarizes the ciprofloxacin resistance genes, the respective mutations/genetic markers, as well as the nucleotide sequences for the selected primers used in our allele-specific primer extension reaction.

TABLE 5

| Ciprofloxacin-resistance Genes | Mutations/Genetic Markers | Allele-Specific Primer Extension Primers |
|---|---|---|
| gyrA | S91P | TCATTTCACAATTCAATTACTCAATACCACCCCCACGGCGATCC (SEQ ID NO: 40) |
| | D95A | TCAATCAATTACTTACTCAAATACCGCCATACGGACGATGGTGG (SEQ ID NO: 41) |
| | D95G | CTTTTCAAATCAATACTCAACTTTCGCCATACGGACGATGGTGCC (SEQ ID NO: 42) |
| | D95N | CTTTCTACATTATTCACAACATTACGCCATACGGACGATGGTGTT (SEQ ID NO: 43) |
| | S91Y | TTACTACACAATATACTCATCAATTACCACCCCCACGGCGATTA (SEQ ID NO: 44) |
| | S91F | TCAATCATTACACTTTTCAACAATTACCACCCCCACGGCGATTT (SEQ ID NO: 45) |
| | D95Y | CAATTCATTTCATTCACAATCAATGCCATACGGACGATGGTGTA (SEQ ID NO: 46) |
| parC | D86N | ATACCAATAATCCAATTCATATCAGTAAATACCATCCGCACGGCA (SEQ ID NO: 47) |
| | S87R | TACAAATCATCAATCACTTTAATCTACCATCCGCACGGCGACC (SEQ ID NO: 48) |
| | S87N | CAATTTCATCATTCATTCATTTCAACCATCCGCACGGCGACAA (SEQ ID NO: 49) |
| | S88P | CAATAAACTATACTTCTTCACTAACATCCGCACGGCGACAGTC (SEQ ID NO: 50) |
| | E91K | TTCACTTTTCAATCAACTTTAATCCCATGCGCACCATCGCCTT (SEQ ID NO: 51) |
| | E91G | CTTTCAATTACAATACTCATTACACCATGCGCACCATCGCCC (SEQ ID NO: 52) |
| mtrR | G45D | TCAACTAACTAATCATCTATCAATTTTGAAATGCCAATAGAGCGCGT (SEQ ID NO: 33) |
| | G45S | AATCAATCTTCATTCAAATCATCATTTGAAATGCCAATAGAGCGCGCT (SEQ ID NO: 34) |
| | -35del | TAATCTTCTATATCAACATCTTACTTATACATACACGAATTGCACGGATAAAAA (SEQ ID NO: 35) |
| | -10insTT | CTTTTACAATACTTCAATACAATCGGTTTGACGAGGGCGGATTATAAAAAG (SEQ ID NO: 36) |

Table 6 summarizes the cephalosporin resistance genes, the respective mutations/genetic markers, as well as the nucleotide sequences for the selected primers used in our allele-specific primer extension reaction.

TABLE 6

| Cephalosporin-resistance Genes | Mutations/Genetic Markers | Allele-Specific Primer Extension Primers |
|---|---|---|
| penA | G545S | TTCAATCATTCAAATCTCAACTTTGCCGACTGCAAACGGTTACTACA (SEQ ID NO: 53) |

Table 7 summarizes the azithromycin resistance genes, the respective mutations/genetic markers, as well as the nucleotide sequences for the selected primers used in our allele-specific primer extension reaction.

TABLE 7

| Azithromycin-resistance Genes | Mutations/Genetic Markers | Allele-Specific Primer Extension Primers |
|---|---|---|
| mtrR | G45D | TCAACTAACTAATCATCTATCAATTTTGAAATGCCAATAGAGCGCGT (SEQ ID NO: 33) |
| | G45S | AATCAATCTTCATTCAAATCATCATTTGAAATGCCAATAGAGCGCGCT (SEQ ID NO: 34) |
| | -35delA | TAATCTTCTATATCAACATCTTACTTATACATACACGATTGCACGGATAAAAA (SEQ ID NO: 35) |
| | -10insTT | CTTTTACAATACTTCAATACAATCGGTTTGACGAGGGCGGATTATAAAAAG (SEQ ID NO: 36) |

Table 8 summarizes the spectinomycin resistance genes, the respective mutations/genetic markers, as well as the nucleotide sequences for the selected primers used in our allele-specific primer extension reaction.

TABLE 8

| Spectinomycin-resistance Genes | Mutations/ Genetic Markers | Allele-Specific Primer Extension Primers |
|---|---|---|
| 16S rRNA | G1064C | TTACTCAAAATCTACACTTTTTCAAACATCTCACGACA CGAGCTGAG (SEQ ID NO: 54) |
| | C1192U | CTTTTCATCTTTTCATCTTTCAATATAAGGGCCATGAG GACTTGACG (SEQ ID NO: 55) |

Example 5

Multiplex Allele-Specific Primer Extension Reactions

Using the selected primers (Example 4), we performed multiplex allele-specific primer extension reactions. The allele-specific primer extension reaction was performed in a single vessel, which contained a total volume of 20 µl. The multiplex allele-specific reactions contained 1×PCR buffer (Invitrogen, CA), 1.25 mM MgCl$_2$, 100 nM of each primer, 5 µM dATP, dTTP, dGTP (Invitrogen, CA), 5 µM biotin-dCTP (Invitrogen, CA), 1 U of Tsp DNA polymerase (Invitrogen, CA), and 5 µl of purified multiplex PCR products from all four (4) multiplex PCRs as templates.

Thermal cycling conditions for extension reactions were performed in a Biometra 3.0 PCR System (Biometra, Germany) programmed for an initial cycle of 1 min at 95° C. followed by 35 cycles of 30 sec at 95° C., 30 sec at 55° C., and 30 sec at 72° C. A final 10 min extension step was performed at 72° C.

Example 6

Detection for Allele-Specific Extended Primers

Detection of allele-specific extended primers is indicative of the presence of SNP in the genes examined. Detection of allele-specific extended primers can be achieved by several methodologies. This includes gel electrophoresis, capillary electrophoresis, as well as DNA microarray. In this particular example, we illustrated the use of a DNA microarray. The working principle of a DNA microarray involves the use of microspheres to hybridize and sort out the allele-specific extended primers, and followed by their subsequent detection using an array reader. The presence of fluorescence is indicative of the presence of an allele-specific extended primer, which in turn is indicative of the presence of a SNP in the gene.

A) Hybridization and Sorting

Extended allele-specific primer hybridizations were performed using oligonucleotide-labeled xMAP flow cytometric microspheres (Luminex Corp, TX) in a hybridization buffer containing 0.2 M NaCl, 0.08% sodium lauroylsarcosine, 0.1 M Tris-HCl, pH 8.0, and 4 mM EDTA pH 8.0. Reactions were carried out in a Biometra 3.0 PCR System (Biometra, Germany) programmed for a 3 min melting at 95° C. and a 15 min hybridization at 37° C.

Sorting of allele-specific extended primers hybridized to xMAP microspheres was performed using a Bio-Plex 200 (Bio-Rad, CA) flow cytometry instrument.

B) Detection

1 µl Streptavidin R-phycoerythrin conjugate (SAPE) and 250 µl 1×NaCl hybridization buffer was added to each sorted xMAP microsphere. Microspheres hybridized to allele-specific extended primers containing biotin-dCTP fluoresce and were detected using the Bio-Plex 200 array reader.

Altogether, Examples 1-6 show that we have successfully developed a new diagnostic test screening for thirty (30) genetic markers of antibiotic-resistance in ten (10) *Neisseria gonorrhoeae* genes (28 point mutations in eight (8) chromosomal genes and 2 plasmid genes) and one (1) *Neisseria gonorrhoeae* species-specific marker. The assay employs multiplex PCR amplifying twelve (12) loci in the *Neisseria gonorrhoeae* genome followed by a multiplexed allele-specific primer extension reaction targeting specific antibiotic resistance mutations and genes.

Example 7

Generation of Antibiotic Resistance Profiles Using Six (6) ATCC *Neisseria gonorrhoeae* Strains A) WHO/CDC Characterized *Neisseria gonorrhoeae* Strains After the development of an antibiotic resistance panel assay, we sought to confirm if the assay can properly reveal the antibiotic resistance profile for a particular *Neisseria gonorrhoeae* strain. To this end, we attempted to obtain particular *Neisseria gonorrhoeae* strains that exhibit specific antibiotic resistance behavior. As detailed hereinafter, our panel assay has validated using six (6) *Neisseria gonorrhoeae* ATCC strains.

This example details our efforts to obtain particular *Neisseria gonorrhoeae* strains that exhibit specific antibiotic resistance behavior. Unemo et. al. have phenotypically and genetically characterized eight (8) *Neisseria gonorrhoeae* strains from the World Health Organization surveillance collection in 2009. These strains were intended for assurance of antibiotic susceptibility global quality assurance and quality control of gonococcal antimicrobial resistance surveillance for public health purposes. *J. Antimicrob. Chemother.* 63: 1142-1151). The authors characterized phenotypic antibiotic susceptibility profiles (antibiogram) for these strains and their identification of sequence polymorphisms and plasmids associated with the antibiotic resistance.

To no avail, we were unable to obtain these strains from CDC despite making several request attempts. As an alternative, we obtained from another source (i.e., ATCC) of six (6) characterized *Neisseria gonorrhoeae* strains. Two (2) of the six (6) strains have been characterized: the first is ATCC 31424 which was characterized as beta-lactmase positive (bla); and the second is ATCC 31953 which was characterized as nalidixic acid (i.e., fluoroquinolone) resistant.

Using our antibiotic resistance panel assay, we examined the antibiotic resistance profile in these six (6) *Neisseria gonorrhoeae* strains. The results of the panel assay are presented in graphical format which includes 30 genetic markers (i.e., 28 point mutations in eight (8) chromosomal genes in

*Neisseria gonorrhoeae*, two (2) plasmid genes, as well as 17 alleles in controls). Normal alleles are shown by white bars, mutant alleles, confirming resistance, are shown by black bars (See, FIGS. 3-8).

In these figures, Y axis indicates Measurement Fluorescence Intensity units; and X axis reflects the fluorescence signals from genetic alleles. For most alleles, a value of 250 measurement fluorescence intensity units is established empirically to be the minimal threshold fluorescence intensities (i.e., representing presence or absence of genetic markers).

Figure 5:
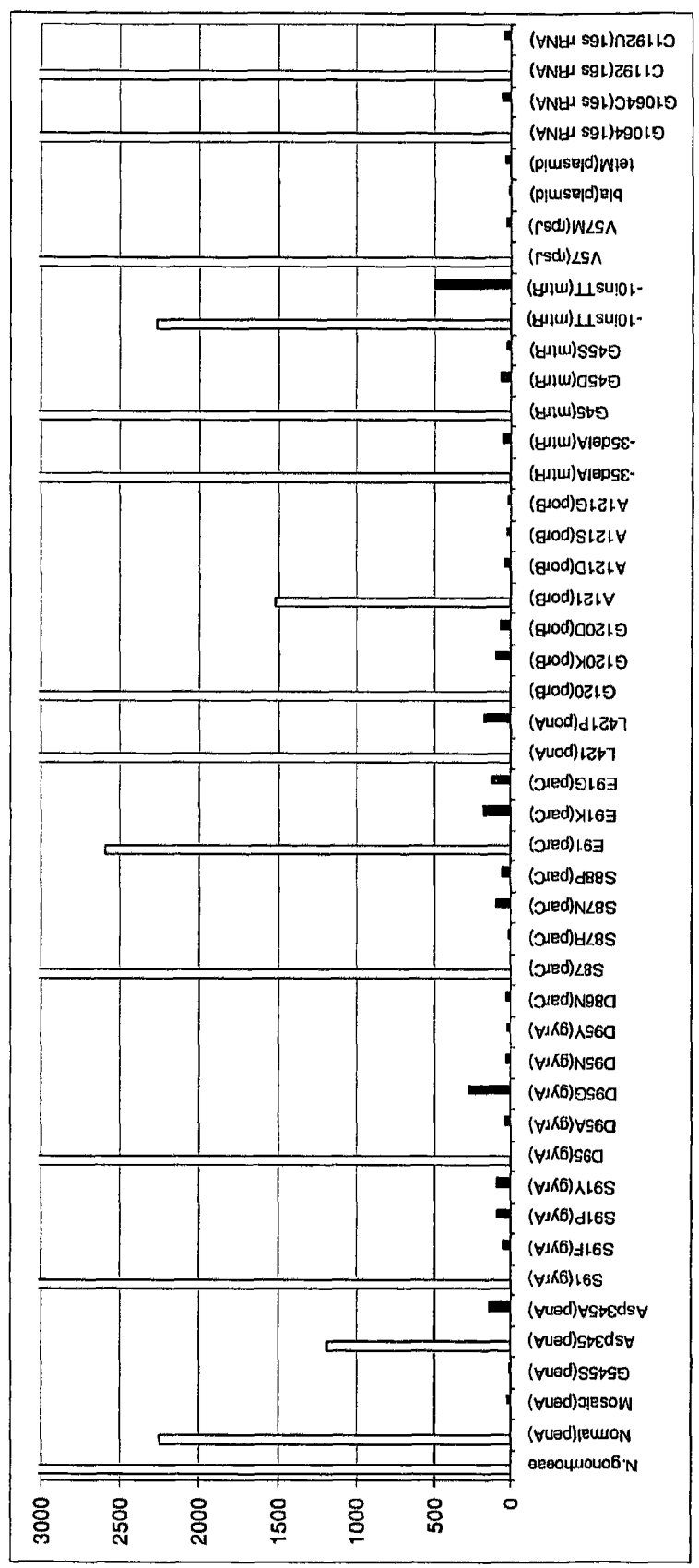
FIG. 5 depicts the profile of antibiotic resistance in *Neisseria gonorrhoeae* strain ATCC 27628. Normal alleles are shown by white bars. Mutant alleles, confirming resistance, are shown by black bars.
Figure 6:
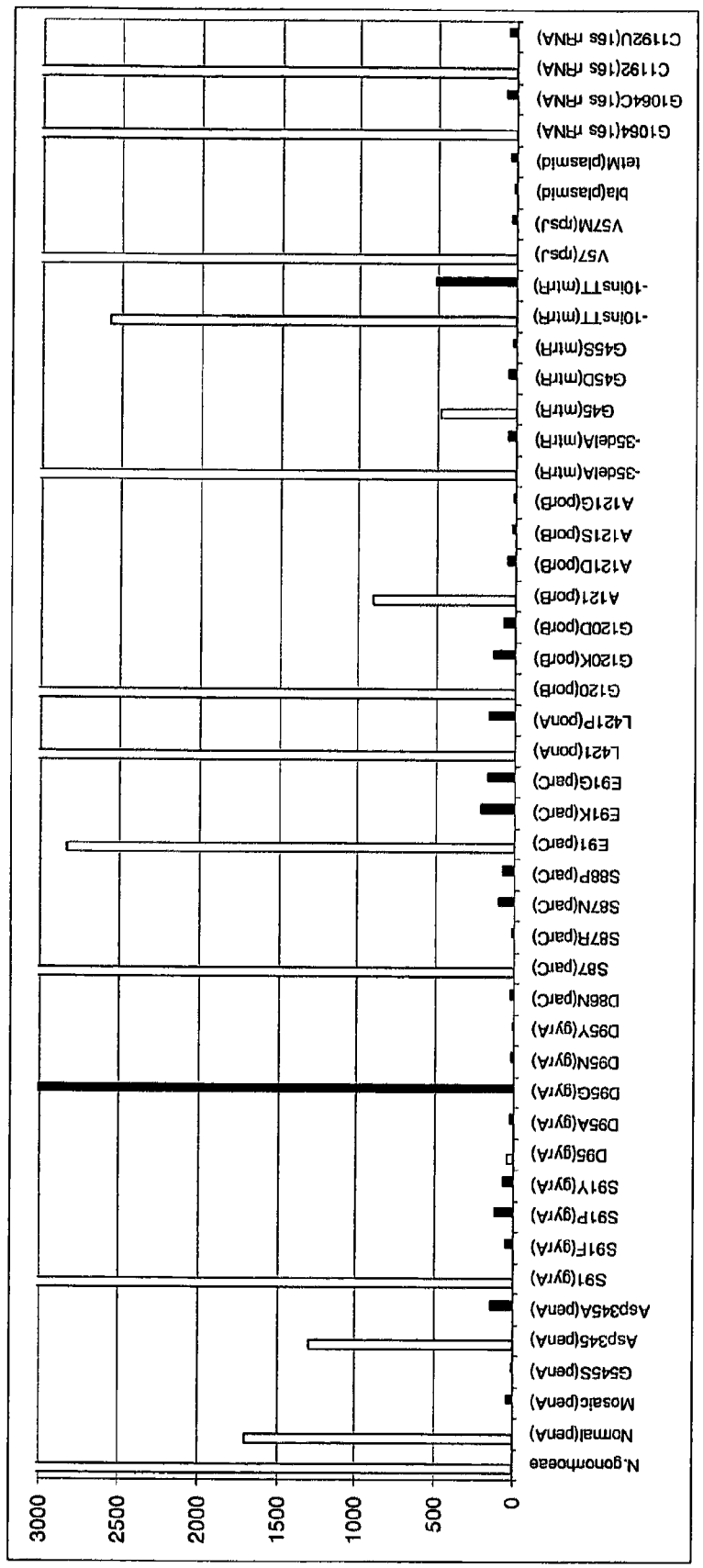
FIG. 6 depicts the profile of antibiotic resistance in *Neisseria gonorrhoeae* strain ATCC 31953. Normal alleles are shown by white bars. Mutant alleles, confirming resistance, are shown by black bars.
Figure 7:
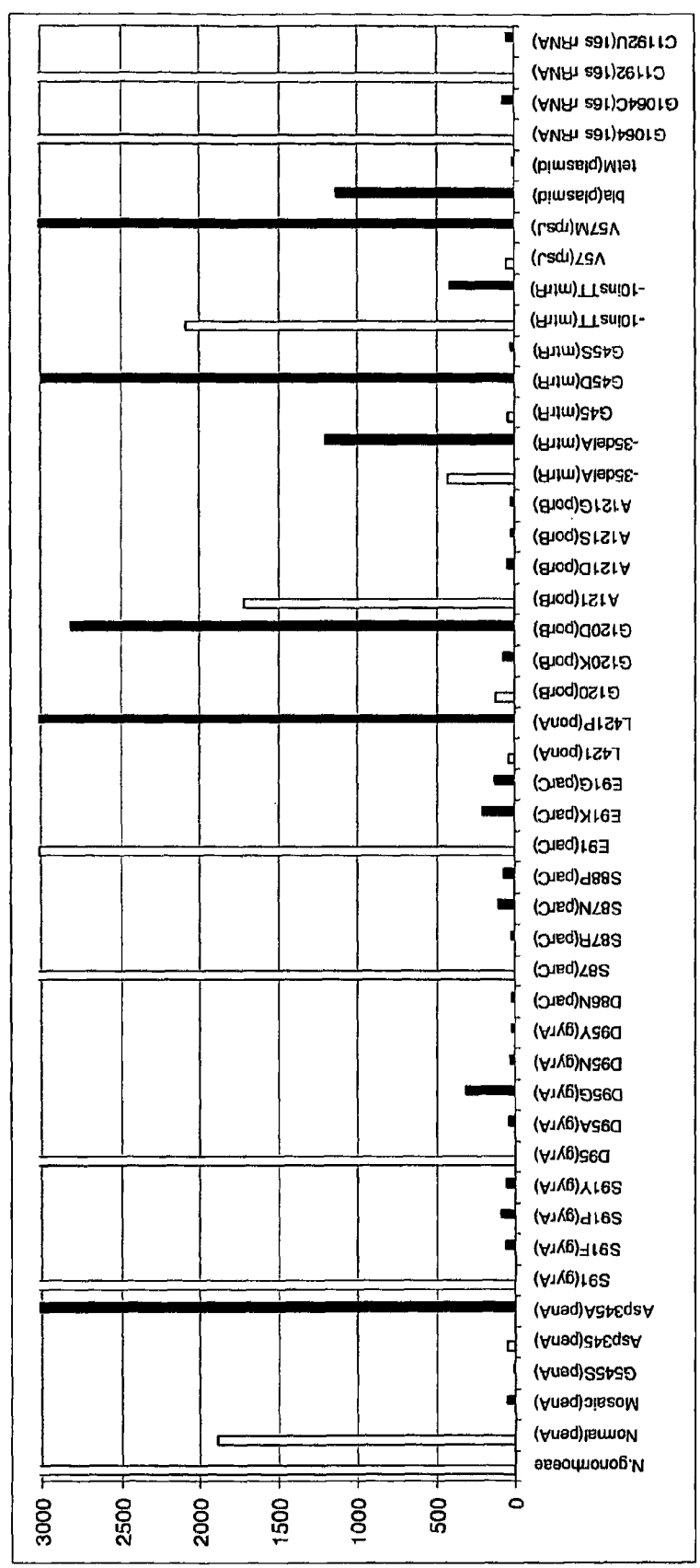
FIG. 7 depicts the profile of antibiotic resistance in *Neisseria gonorrhoeae* strain ATCC 31426. Normal alleles are shown by white bars. Mutant alleles, confirming resistance, are shown by black bars.
Figure 8:
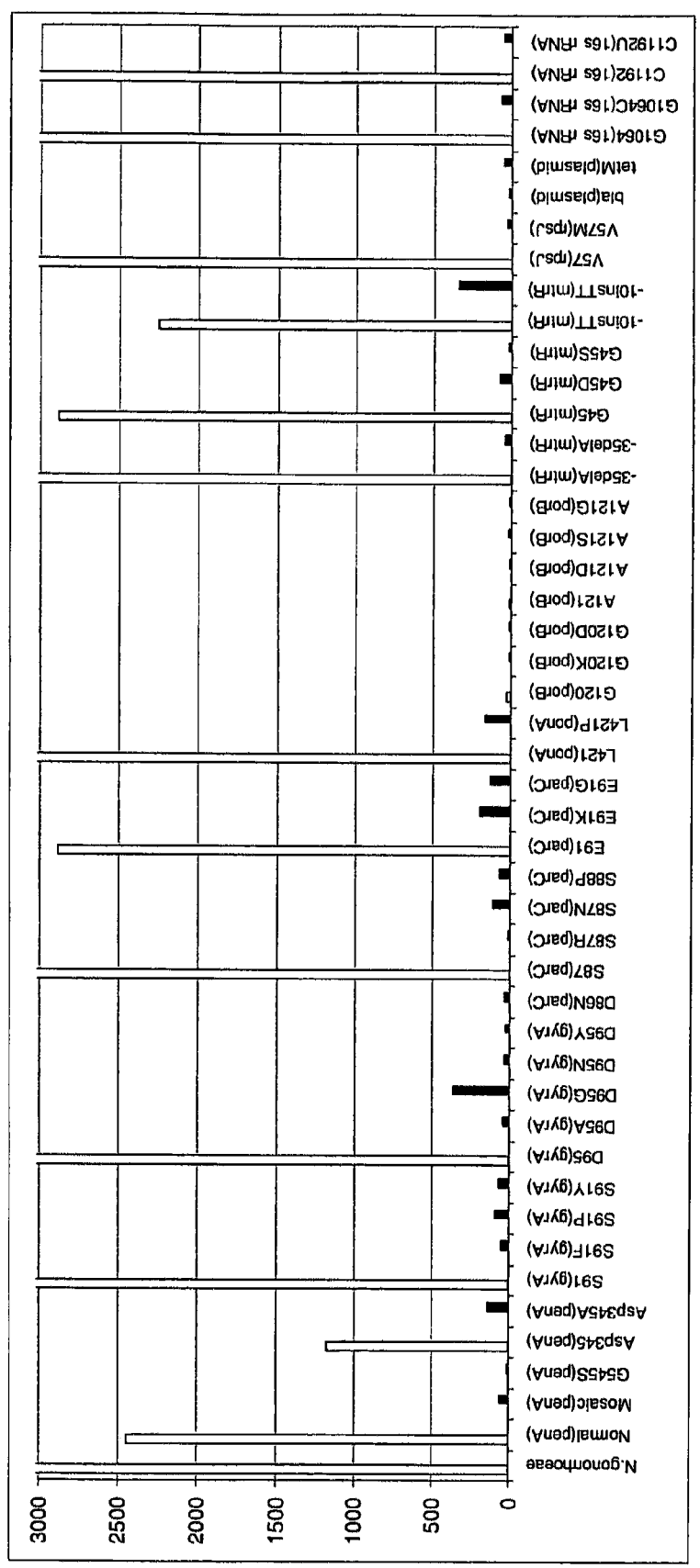
FIG. 8 depicts the profile of antibiotic resistance in *Neisseria gonorrhoeae* strain ATCC 19424. Normal alleles are shown by white bars. Mutant alleles, confirming resistance, are shown by black bars.

As shown in FIGS. 5 and 8, two (2) *Neisseria gonorrhoeae* strains (i.e., ATCC 27628 (FIG. 5) and ATCC 19424 (FIG. 8)) lacked any antibiotic resistance mutations. This data implies that these two (2) ATCC strains are susceptible to all six (6) antibiotics (i.e., penicillin, tetracycline, ciprofloxacin, azithromycin, spectinomycin, and cefixime).

On the other hand, four (4) of the *Neisseria gonorrhoeae* strains (i.e., ATCC 49981, ATCC 49226, ATCC 31953, and ATCC 31426) had a variety of different mutations (see Table 9 below). Antibiotic resistance profiles varied in these strains. Based on the results of our molecular assay, we concluded that the ATCC 49981 and ATCC 31426 strains were resistant to four (4) antibiotics (i.e., penicillin, tetracycline, ciprofloxacin, azithromycin). The ATCC 49226 strain was resistant to penicillin. The ATCC 31953 strain was resistant to ciprofloxacin. Therefore, the present antibiotic resistance panel assay accurately reveals the antibiotic resistance profile for all these six (6) *Neisseria gonorrhoeae* strains.

Table 9 summarizes the antibiotic resistance profile for the six (6) *Neisseria gonorrhoeae* strains obtained from ATCC. The antibiotic resistance in these strains has been previously characterized by ATCC. Table 9 summarizes the comparison between the phenotypic characterization by ATCC and the antibiotic resistance profile generated from our assay.

Example 8

Generation of Antibiotic Resistance Profiles Using Three (3) Clinical Samples

The present panel assay works well when ATCC *Neisseria gonorrhoeae* strains were used. In this example, we presented our findings using clinical samples. To this end, we conducted an initial experiment using three (3) DNA samples originating from cervicovaginal swabs taken from individuals who visited gynecologist offices. Then we expanded this study by using forty (40) additional clinical specimens. The results of the later expanded study confirm the earlier initial findings.

In the initial experiment, we obtained three (3) samples. Cervicovaginal swabs were obtained using OneSwab® technology. Clinical samples were processed and DNA from the clinical samples was extracted using standard extraction procedure (i.e., guanidine thiocyanate). To ensure that the clinical samples contained *Neisseria gonorrhoeae*, we performed a real-time PCR assay using specific probes to detect *Neisseria gonorrhoeae*. The details of our real-time PCR assay have been previously reported (protocol slightly modified from Ho et al. *J. Clin. Pathol.* (1992); 45: 439-442).

Figure 9:
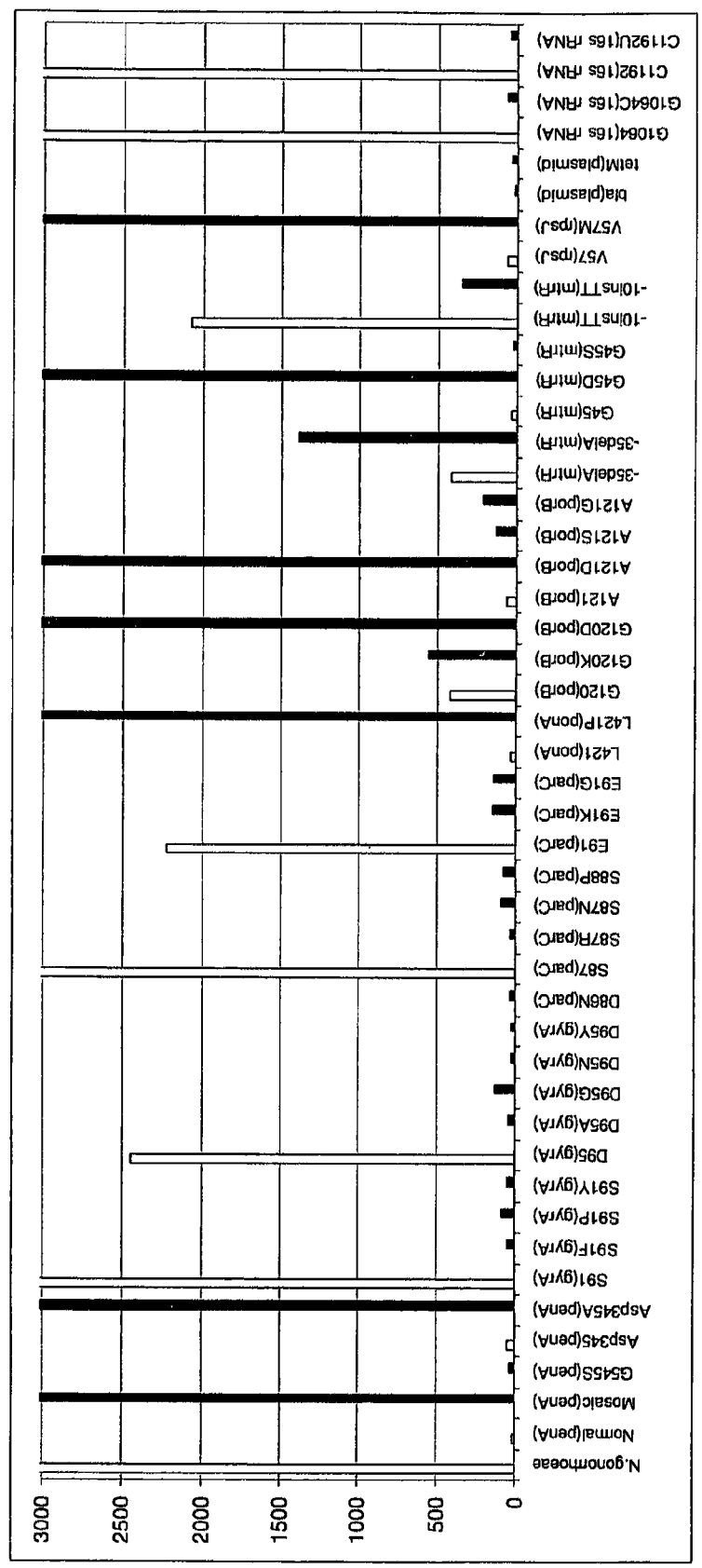
FIG. 9 depicts the profile of antibiotic resistance in *Neisseria gonorrhoeae* obtained from a cervicovaginal swab sample (clinical sample 1). Normal alleles are shown by white bars. Mutant alleles, confirming resistance, are shown by black bars.

The presence of *Neisseria gonorrhoeae* in all three (3) clinical samples were confirmed using our panel assay in which porA was used as a *Neisseria gonorrhoeae* species-specific marker. Our panel assay reveals mutations in the penA, ponA, porB, mtrR, and rpsJ genes (See, FIG. 9). This implies *Neisseria gonorrhoeae* strain infecting this particular individual has an intermediate level of antibiotic resistance against penicillin, tetracycline, ciprofloxacin, and azithromycin. Based on this panel finding, we recommend that penicillin, tetracycline, ciprofloxacin, azithromycin should not be used for treatment of gonorrhea infection in this individual. Rather, spectinomycin and cephalosporin are recommended.

TABLE 9

| Neisseria gonorrhoeae strains | Antibiotic Resistance Characterization by ATCC | Mutations/Genetic Markers Detected by our Assay | Antibiotic Resistance Profile Using our Assay |
|---|---|---|---|
| ATCC 49981 | No information provided by ATCC | Mosaic (penA), Asp345A (penA), G45S (mtrR), V57M (rpsJ), bla (plasmid). | Resistant to: penicillin, tetracycline, ciprofloxacin, azithromycin |
| ATCC 49226 | No information provided by ATCC | Mosaic (penA), Asp345A (penA), V57M (rpsJ). | Resistant to penicillin |
| ATCC 27628 | No information provided by ATCC | No mutations/genetic markers were detected | No antibiotic resistance |
| ATCC 31953 | Resistant to: nalidixic acid and streptomycin[§] | D95G (gyrA) | Resistant to ciprofloxacin |
| ATCC 31426 | Resistant to Beta-lactams (i.e., bla positive) | Asp345A (penA), L421P (porA), G120D (porB), -35delA (mtrR), G45D (mtrR), V57M (rpsJ), bla (plasmid). | Resistant to: penicillin, tetracycline, ciprofloxacin, azithromycin |
| ATCC 19424 | No information provided by ATCC | No mutations/genetic markers were detected | No antibiotic resistance |

[§]Note that nalidixic acid and ciprofloxacin belong to the fluoroquinolone class of antibiotics. The observed cross-resistance between nalidixic acid and ciprofloxacin occurs frequently. Streptomycin is not included in the *Neisseria gonorrhoeae* antibiotic resistance assay.

Figure 10:
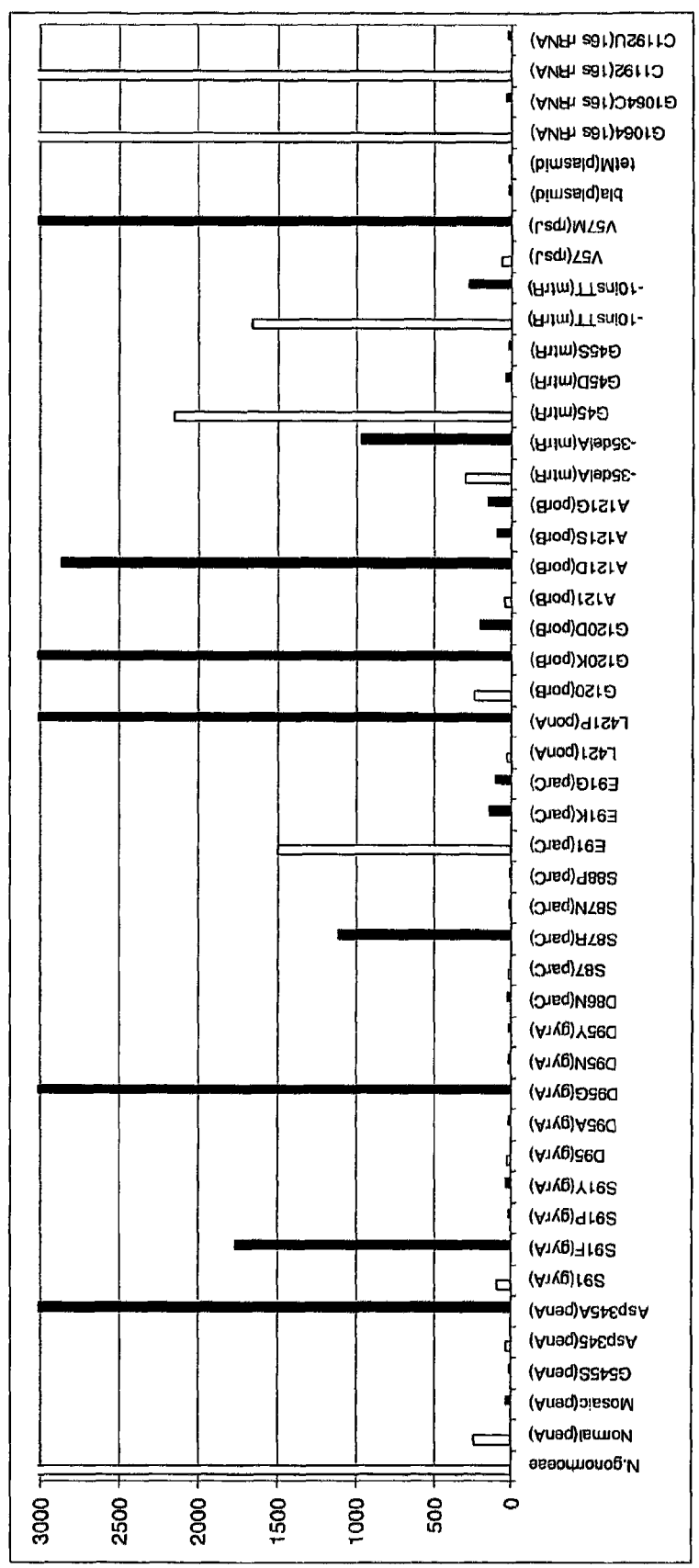
FIG. 10 depicts the profile of antibiotic resistance in *Neisseria gonorrhoeae* obtained from a cervicovaginal swab sample (clinical sample 2). Normal alleles are shown by white bars. Mutant alleles, confirming resistance, are shown by black bars.

In the clinical sample 2, we confirmed positive for *Neisseria gonorrhoeae* based on the presence of porA. Our panel assay reveals mutations in penA, gyrA, ponA, parC, porB, mtrR, and rpsJ genes (See, FIG. 10). This result implies that *Neisseria gonorrhoeae* strain infecting this particular individual has a high level of resistance to penicillin and ciprofloxacin and an intermediate level of resistance to tetracycline and azithromycin. Based on this panel finding, we recommend that penicillin, ciprofloxacin, tetracycline and azithromycin should not be used for treatment of gonorrhea infection in this individual. Rather, spectinomycin and cephalosporin are recommended.

Figure 11:
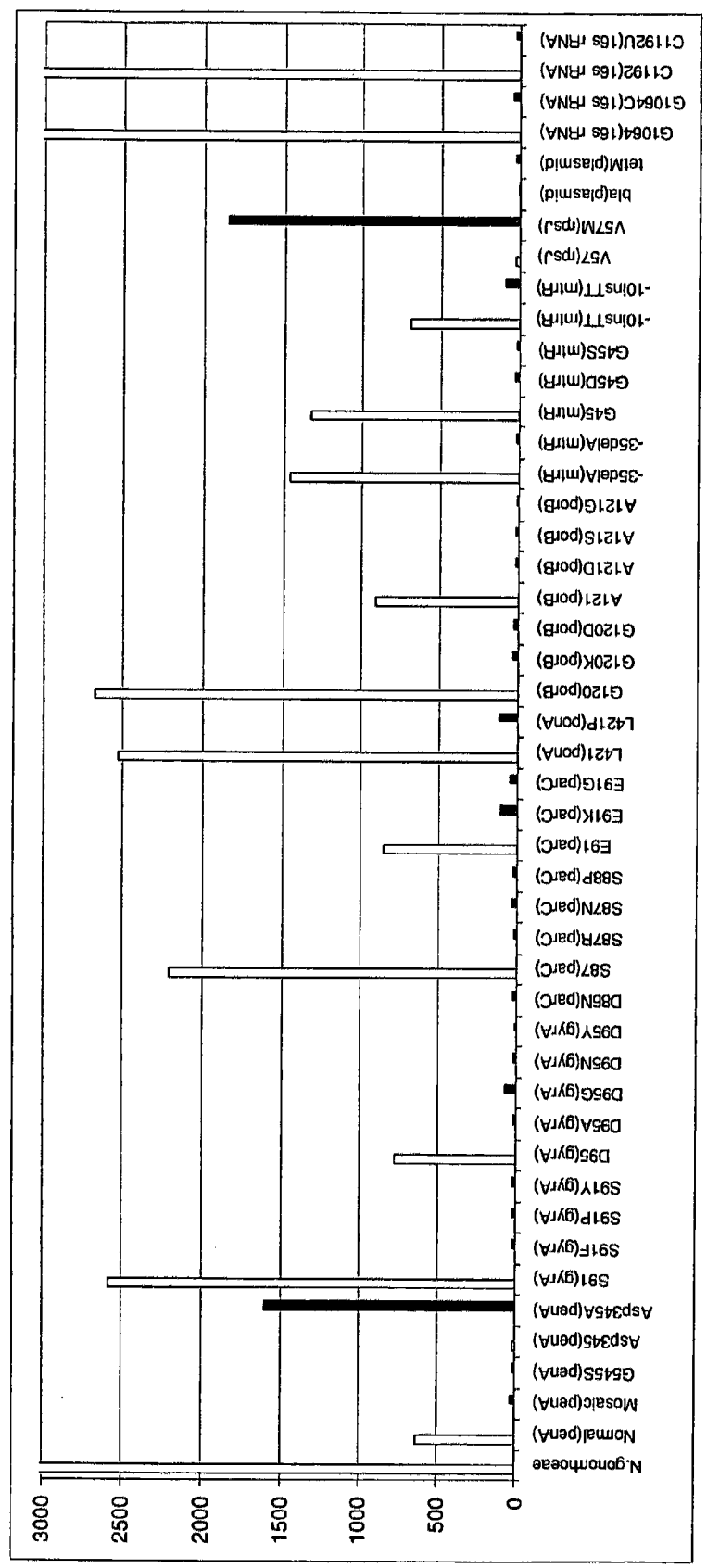
FIG. 11 depicts the profile of antibiotic resistance in *Neisseria gonorrhoeae* obtained from a cervicovaginal swab sample (clinical sample 3). Normal alleles are shown by white bars. Mutant alleles, confirming resistance, are shown by black bars.
Figure 12:
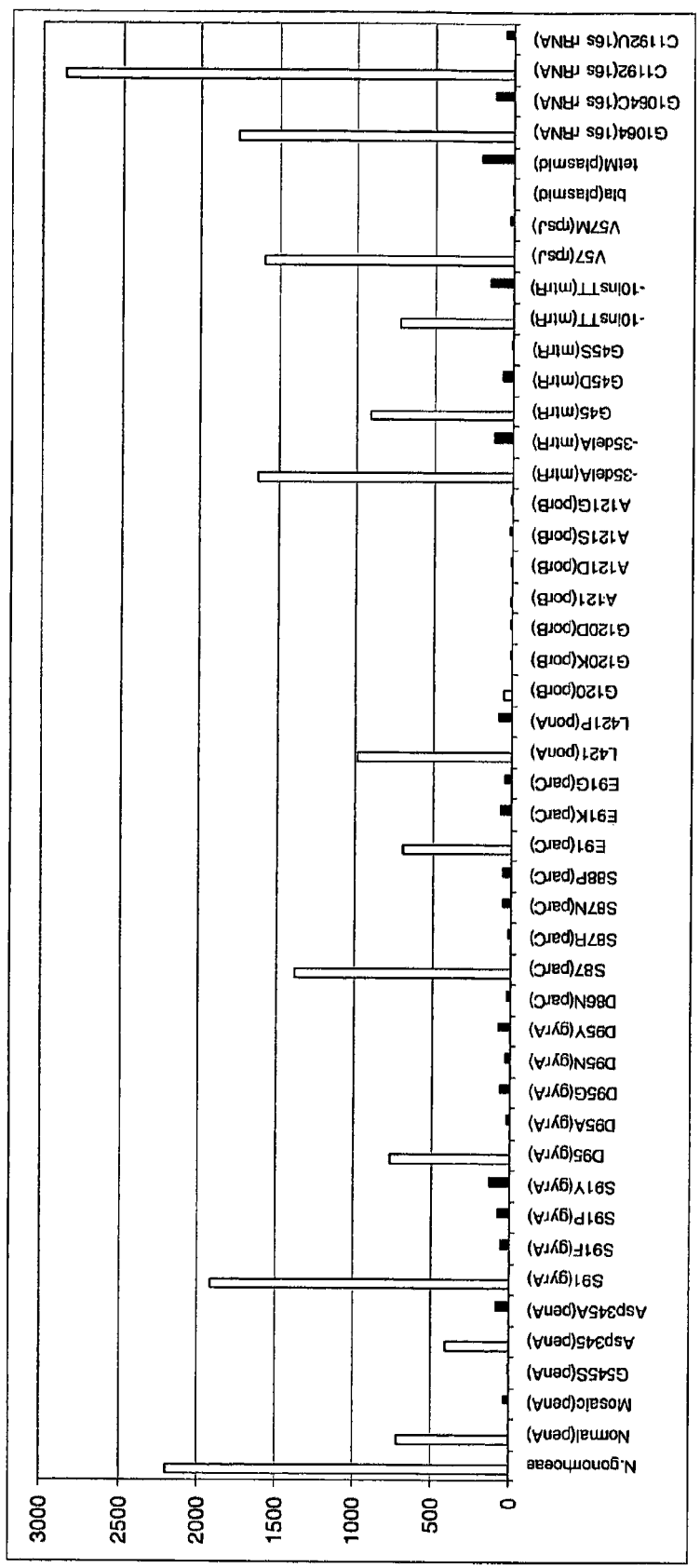
FIG. 12 depicts the profile of antibiotic resistance in *Neisseria gonorrhoeae* strain ATCC 19424. Normal alleles are shown by white bars. Mutant alleles, confirming resistance, are shown by black bars.
Figure 13:
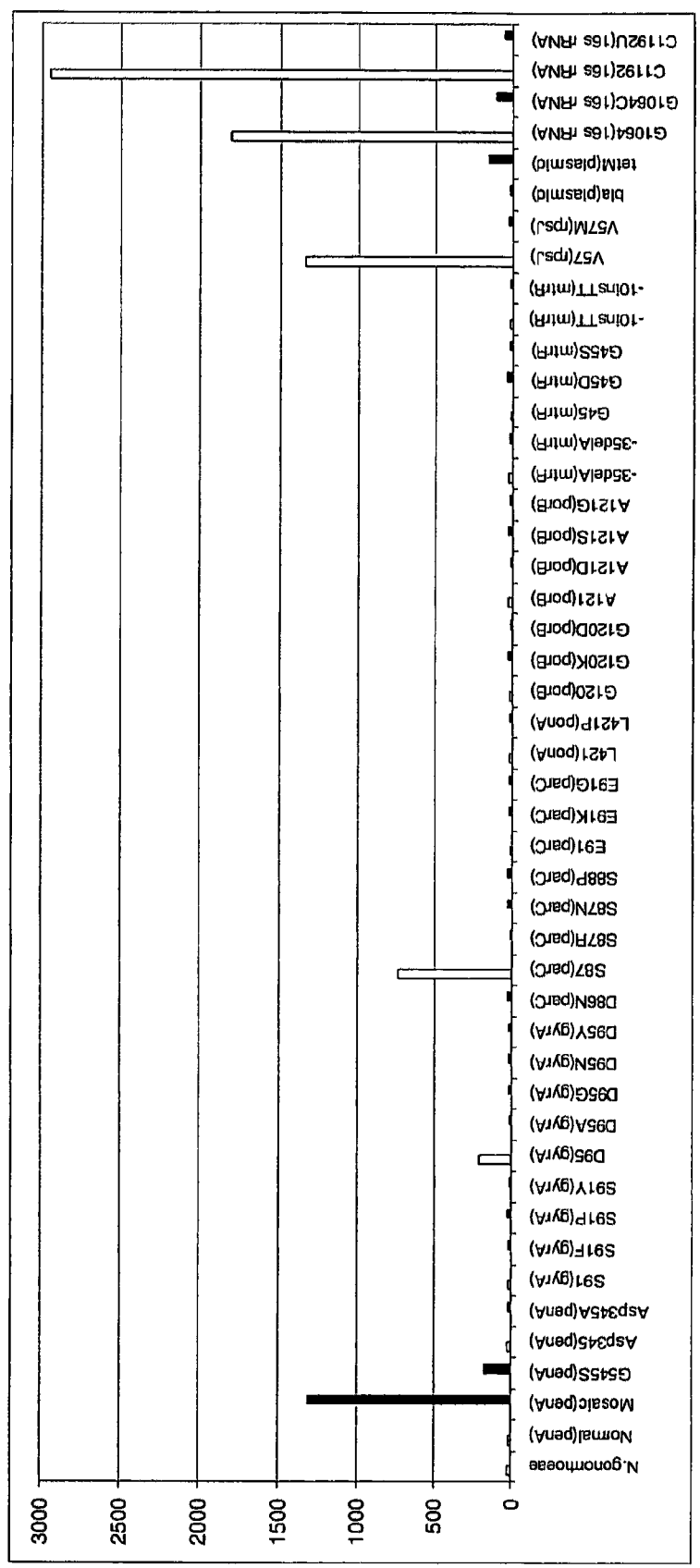
FIG. 13 depicts the profile of antibiotic resistance in *Neisseria mucosa* strain ATCC 25996. Normal alleles are shown by white bars. Mutant alleles, confirming resistance, are shown by black bars. No *Neisseria gonorrhoeae*-specific signal was generated based on PCR amplification and allele-specific primer extension of the *Neisseria gonorrhoeae* species-specific porA gene.
Figure 14:
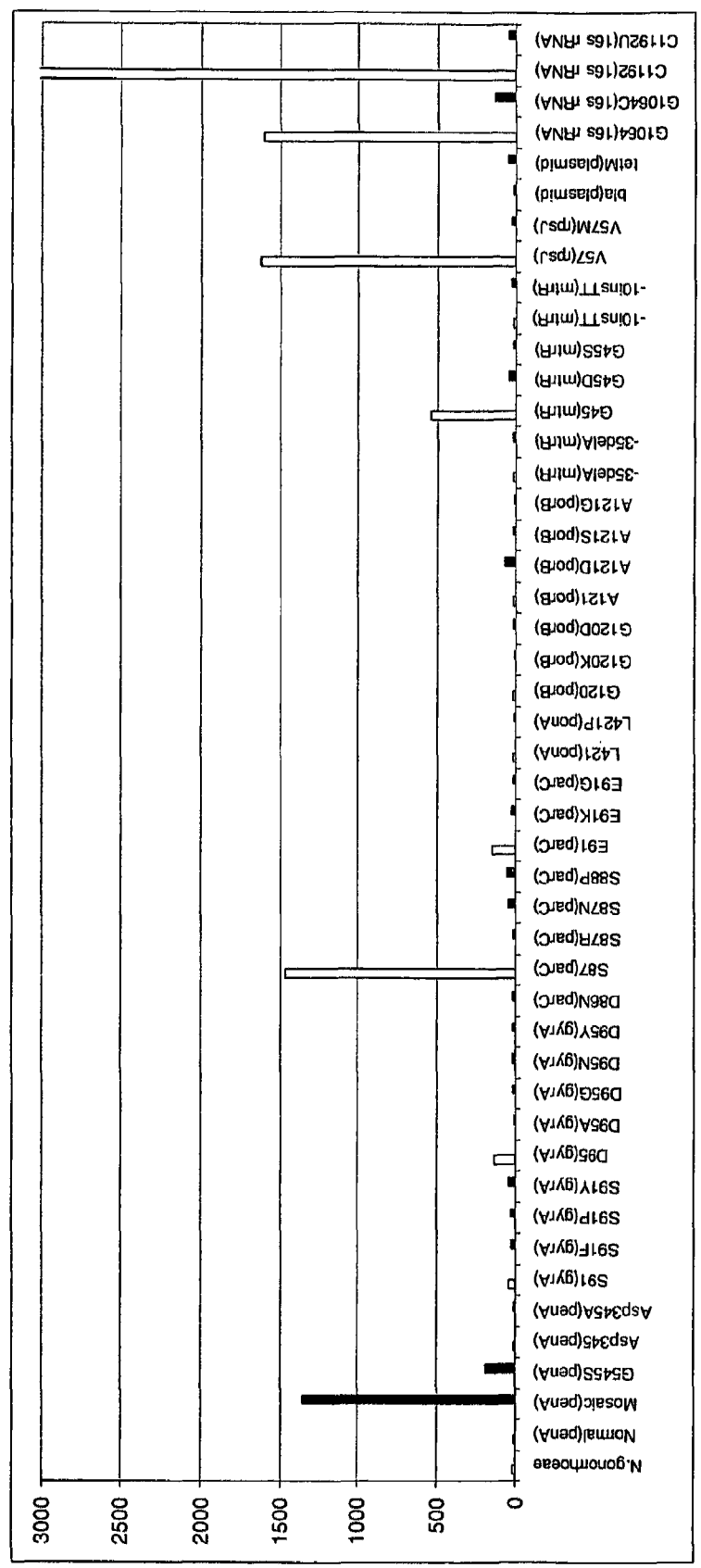
FIG. 14 depicts the profile of antibiotic resistance in *Neisseria cinerea* strain ATCC 14685. Normal alleles are shown by white bars. Mutant alleles, confirming resistance, are shown by black bars. No *Neisseria gonorrhoeae*-specific signal was generated based on PCR amplification and allele-specific primer extension of the *Neisseria gonorrhoeae* species-specific porA gene.
Figure 15:
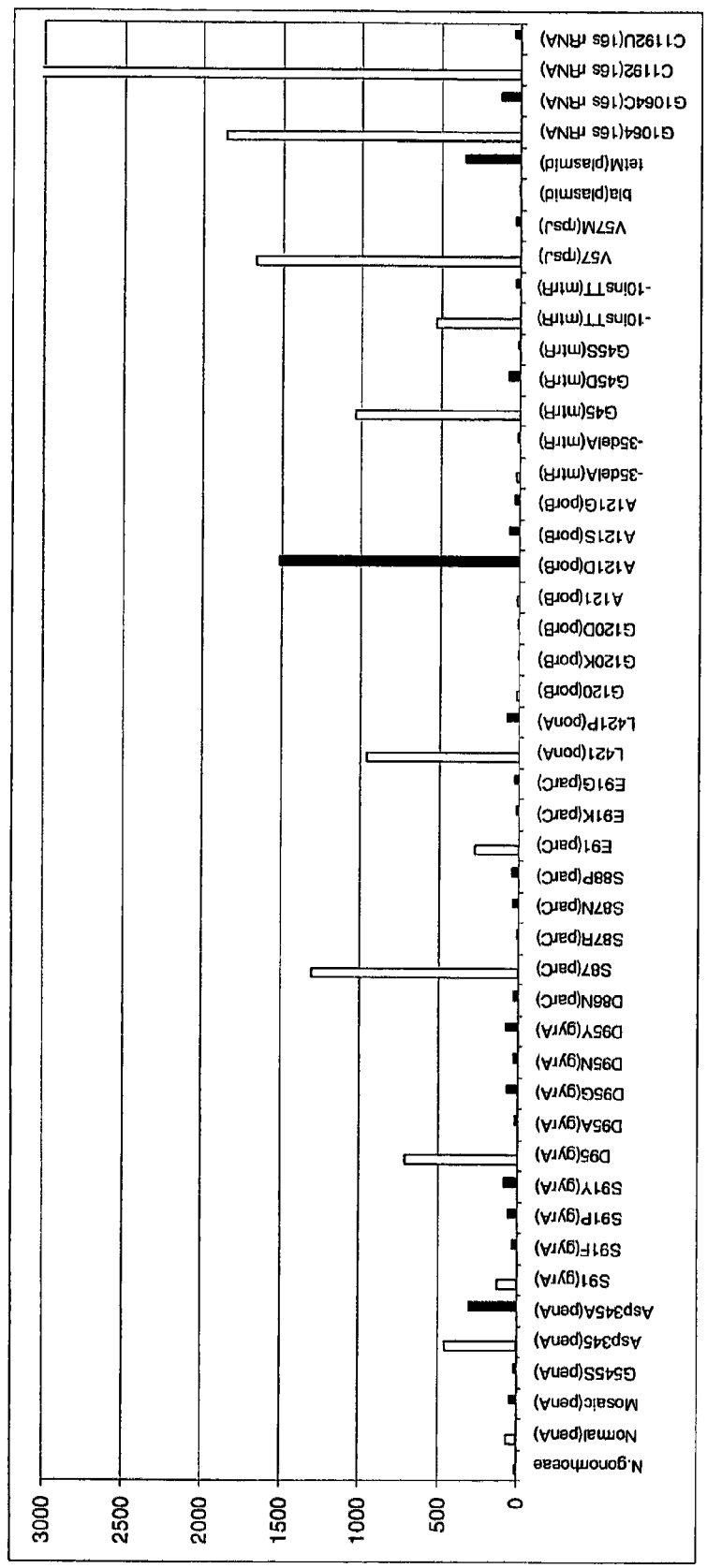
FIG. 15 depicts the profile of antibiotic resistance in *Neisseria meningitidis* strain ATCC 13102. Normal alleles are shown by white bars. Mutant alleles, confirming resistance, are shown by black bars. No *Neisseria gonorrhoeae*-specific signal was generated based on PCR amplification and allele-specific primer extension of the *Neisseria gonorrhoeae* species-specific porA gene.
Figure 16:
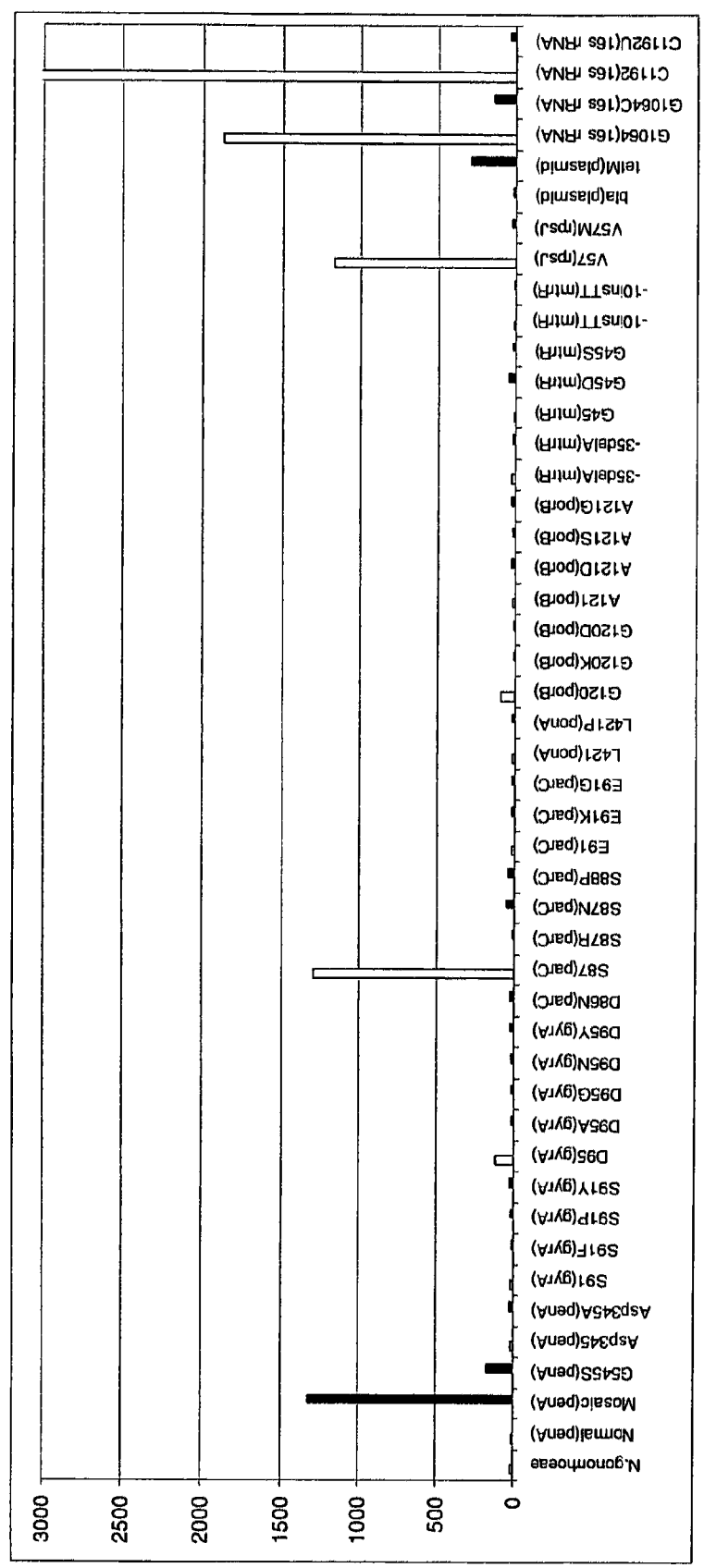
FIG. 16 depicts the profile of antibiotic resistance in *Neisseria sicca* strain ATCC 29256. Normal alleles are shown by white bars. Mutant alleles, confirming resistance, are shown by black bars. No *Neisseria gonorrhoeae*-specific signal was generated based on PCR amplification and allele-specific primer extension of the *Neisseria gonorrhoeae* species-specific porA gene.
Figure 17:
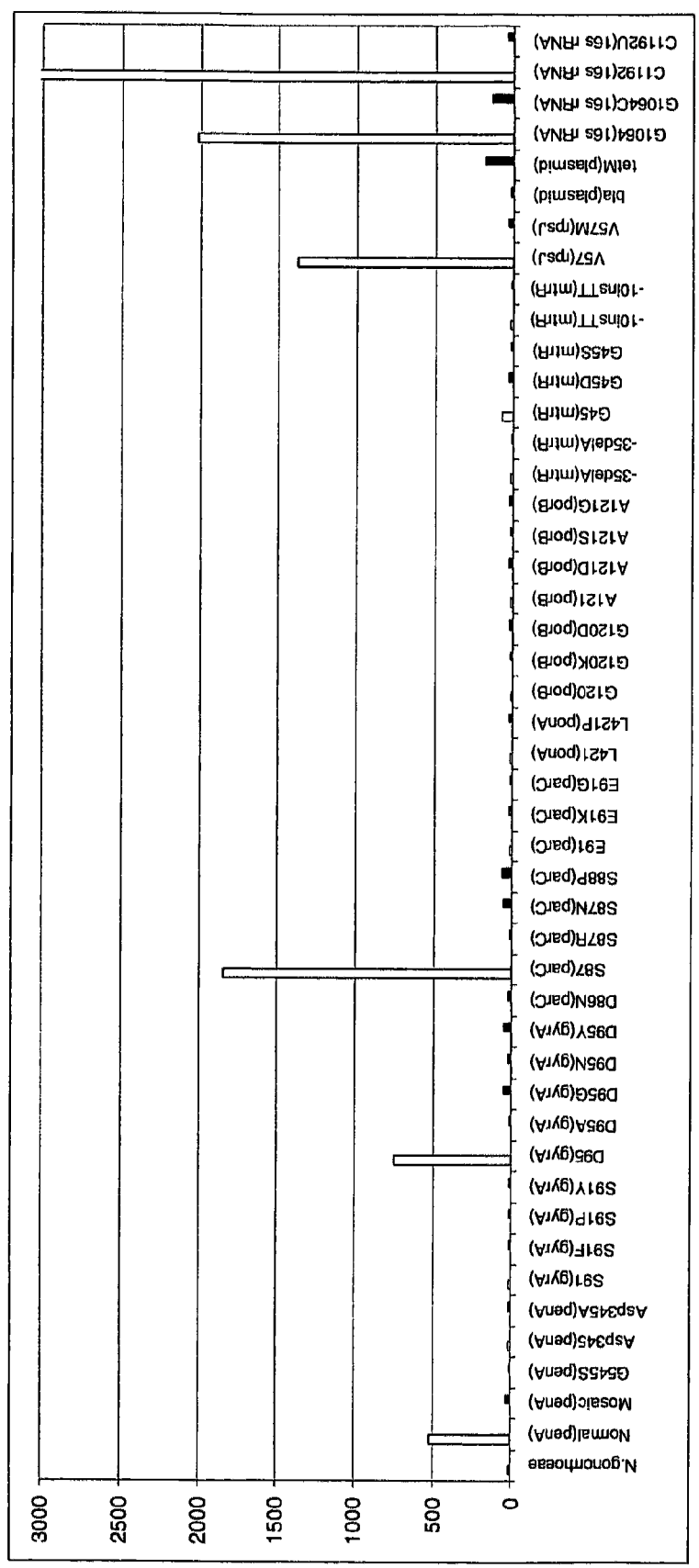
FIG. 17 depicts the profile of antibiotic resistance in *Neisseria perflava* strain ATCC 10555. Normal alleles are shown by white bars. Mutant alleles, confirming resistance, are shown by black bars. No *Neisseria gonorrhoeae*-specific signal was generated based on PCR amplification and allele-specific primer extension of the *Neisseria gonorrhoeae* species-specific porA gene.
Figure 18:
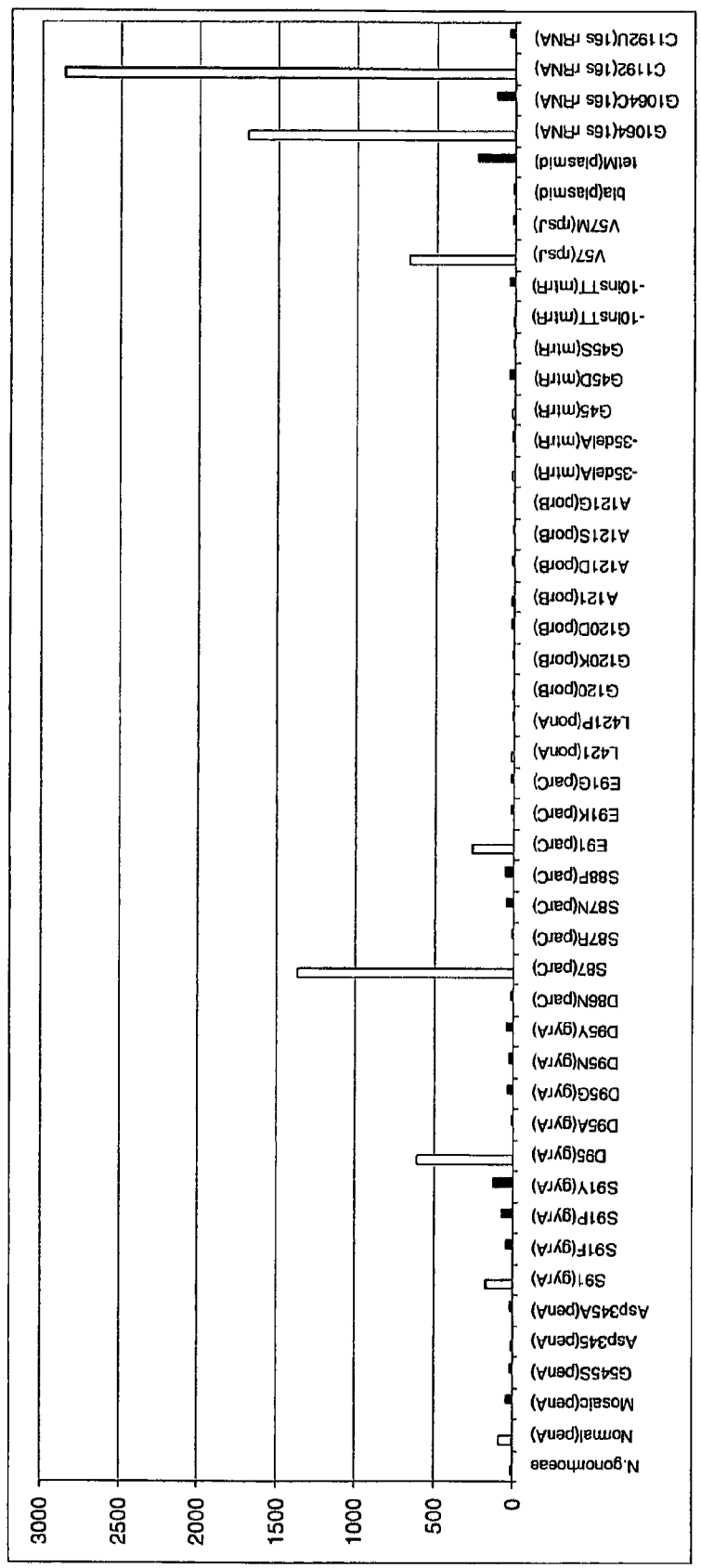
FIG. 18 depicts the profile of antibiotic resistance in *Neisseria flavescens* strain ATCC 13120. Normal alleles are shown by white bars. Mutant alleles, confirming resistance, are shown by black bars. No *Neisseria gonorrhoeae*-specific signal was generated based on PCR amplification and allele-specific primer extension of the *Neisseria gonorrhoeae* species-specific porA gene.
Figure 19:
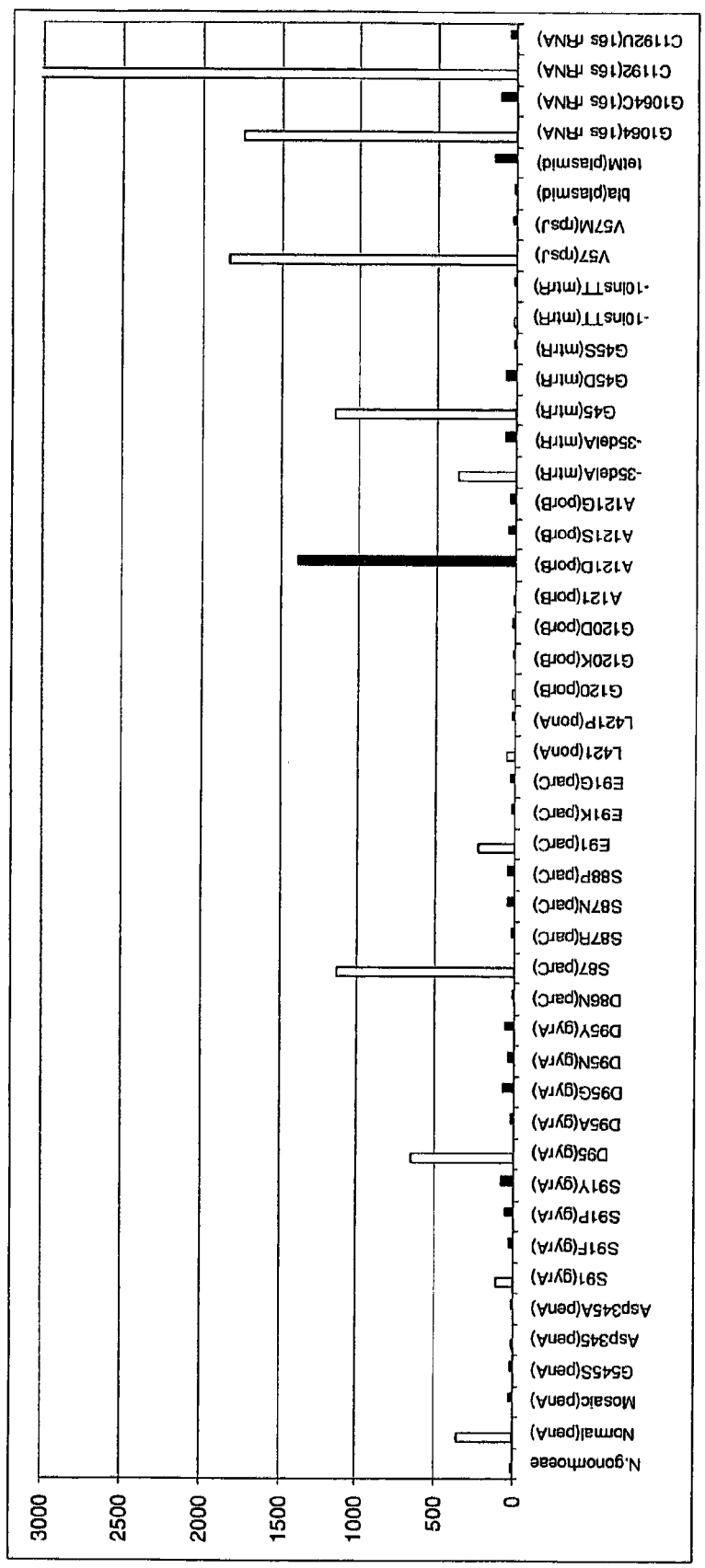
FIG. 19 depicts the profile of antibiotic resistance in *Neisseria lactamica* strain ATCC 23970. Normal alleles are shown by white bars. Mutant alleles, confirming resistance, are shown by black bars. No *Neisseria gonorrhoeae*-specific signal was generated based on PCR amplification and allele-specific primer extension of the *Neisseria gonorrhoeae* species-specific porA gene.
Figure 20:
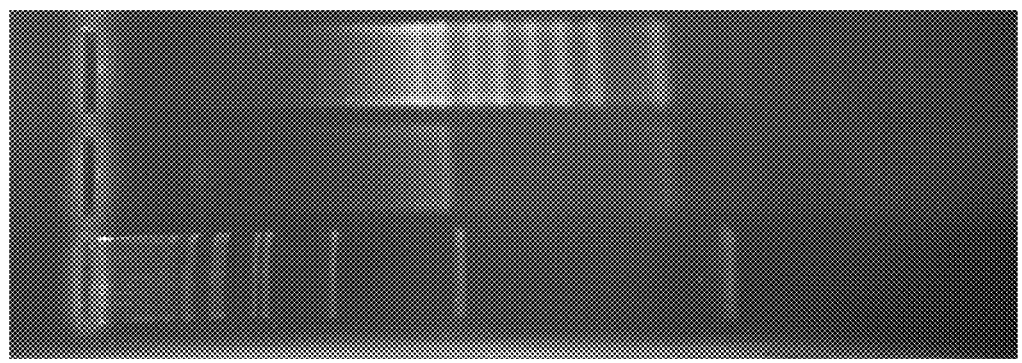
FIG. 20 depicts an agarose gel containing amplicons from multiplex PCR amplifications of all ten (10) *Neisseria gonorrhoeae* chromosomal genetic markers in a single reaction vessel. Lane 1 contains a 100 bp DNA size standard (USB/Affymetrix, CA). Lane 2 contains amplicons from a multiplex PCR amplification employing 100 pg of *Neisseria gonorrhoeae* DNA as a template. Lane 3 contains amplicons from a multiplex PCR amplification employing 10 ng of *Neisseria gonorrhoeae* DNA as a template.

In the clinical sample 3, we also confirmed positive for *Neisseria gonorrhoeae* presence (porA marker). Our panel assay reveals mutations in penA and rpsJ genes (See, FIG. 11), implying that *Neisseria gonorrhoeae* strain infecting this particular individual has a low level of resistance to penicillin and tetracycline. Based on this panel finding, we recommend that penicillin and tetracycline should be avoided for treatment of gonorrhea infection in this individual. Rather, ciprofloxacin, azithromycin, spectinomycin and cephalosporin are recommended.

These results confirm that our antibiotic resistance panel assay can be used to reliably detect antibiotic resistance in *Neisseria gonorrhoeae* from clinical samples. The test results were found to be 100% concordance with *Neisseria gonorrhoeae* real-time PCR test previously performed on the same samples. The present panel assay has advantages of revealing antibiotic resistance profiles against six (6) antibiotics. Our data show that this antibiotic resistance profile differ among the three (3) clinical samples, meaning that all three (3) infecting *Neisseria gonorrhoeae* strains had different antibiotic resistance profile. Based on the present panel assay, recommendations on antibiotic treatment for gonorrhea infection can be set forth to physicians.

Example 9

Frequency of Antibiotic Resistance Mutations in *Neisseria gonorrhoeae* from Forty (40) Clinical Samples We expanded the clinical study and included forty (40) clinical cervicovaginal samples previously diagnosed positive for *Neisseria gonorrhoeae* by qPCR. Using the present panel assay (as listed in Table 1), thirty-nine (39) out of forty (40) *Neisseria gonorrhoeae* samples produced reliable readout with 97% concordance to qPCR results. Thirty-seven (37) out of thirty-nine (39) *Neisseria gonorrhoeae*-positive samples (95%) had at least one chromosomal antibiotic resistance mutation.

The most frequent changes identified were gene rearrangements in penA gene predictive of resistance to penicillin (in 37 out of 40 samples) as well as mutation in rpsJ gene conferring resistance to tetracycline (in 24 out of 40 samples). Ciprofloxacin, penicillin, and azithromycin resistance mutations in genes mtrR (in 13 out of 40 samples), penB (in 13 out of 40 samples), ponA (in 11 out of 40 samples), gyrA (in 3 out of 40 samples), and parC (in 3 out of 40 samples) were also detected.

We did not observe any cephalosporin resistance or spectinomycin resistance mutations in penA and 16s rRNA genes respectively. One (1) tetracycline resistance plasmid containing tet(M) gene was identified. No beta-lactamase producing plasmids were found. Analytical sensitivity of the assay was established to be 25 femtograms of *Neisseria gonorrhoeae* chromosomal DNA which corresponds to about ten (10) genomic copies per PCR. Specificity of the assay was confirmed by performing PCR against eight (8) different *Neisseria* species as well as eight (8) *Neisseria gonorrhoeae*-negative OneSwab® clinical cervicovaginal samples. This data indicate that present panel assay is a powerful tool for screening known antibiotic resistance genetic markers in *Neisseria gonorrhoeae* and predicting clinical resistance in this pathogen.

Table 10 summarizes the genetic markers of antibiotic resistance in *Neisseria gonorrhoeae* identified by our assay using forty (40) clinical cervicovaginal samples positively identified by qPCR.

TABLE 10

Genetic markers of antibiotic resistance in *Neisseria gonorrhoeae* identified by our assay using forty (40) clinical cervicovaginal samples positively identified by qPCR

| Gene | No. of Clinical Samples Positive for (Mutations/Genetic Markers) |
|---|---|
| porA | 39 Positive |
| penA | 17 Positive (Mosaic) |
|  | 37 Positive (Asp345A) |
| gyrA | 3 Positive (S91F) |
|  | 3 Positive (D95G) |
| parC | 3 Positive (S87R) |
| ponA | 11 Positive (L421P) |
| penB | 5 Positive (G120K) |
|  | 2 Positive (G120D) |
|  | 5 Positive (A121D) |
|  | 6 Positive (A121S) |
| mtrR | 4 Positive (G45D) |
|  | 5 Positive (−35delA) |
|  | 4 Positive (−10insTT) |
| tet (M) | 1 Positive (tet(M)) |
| rpsJ | 24 Positive (V57M) |
| bla | None Positive |
| 16s rRNA | None Positive |

Example 10

Frequency of Antibiotic Resistance Mutations in *Neisseria gonorrhoeae* from Six Hundred Twenty (620) Clinical Samples We expanded the clinical study and included six hundred twenty (620) clinical cervicovaginal samples previously diagnosed positive for *Neisseria gonorrhoeae* by qPCR. Using the present panel assay (as listed in Table 1), five hundred eighty-three (583) out of six hundred twenty (620) *Neisseria gonorrhoeae* samples produced reliable readouts with 94% concordance to qPCR results. Five hundred thirty-nine (539) out of the five hundred eighty-three (583) *Neisseria gonorrhoea*-positive samples (93%) had at least one chromosomal antibiotic resistance mutation.

The frequent genetic changes identified were gene rearrangements in penA (475 of the 583 samples) which are predictive of resistance to penicillin, as well as a mutation in rpsJ (313 of the 583 samples) which confers resistance to tetracycline. Cefixime, ciprofloxacin, penicillin, tetracycline and azithromycin resistance mutations in genes penA (5 of the 583 samples), mtrR (186 of the 583 samples), penB (220 of the 583 samples), ponA (162 of the 583 samples), gyrA (34 of the 583 samples), parC (33 of the 583 samples) and 16s rRNA (2 of the 583 samples) were also detected. In addition, plasmid-born bla genes (7 of the 583 samples) and plasmid-born tetM genes (24 of the 583 samples) were identified.

Because ciprofloxacin was the drug of choice for gonorrhea treatment until 2006, and cephalosporins are currently recommended for the same purpose by the CDC, we further analyzed the distribution of ciprofloxacin and cefixime (i.e., cephalosporin) mutations.

In all samples harboring gyrA mutations conferring resistance to ciprofloxacin (34 samples), the S91F mutation was linked with either the D95G (28 samples) or the D95A (6 samples) mutation. There was a strong association between gyrA mutations and mutations in rpsJ (V57M), penA (ins345A), and ponA (L421P). In all cases, gyrA ciprofloxacin resistance mutations were accompanied by either the D86N (1 sample), S87N (4 samples), S87R (28 samples) or E91G (1 sample) mutation in parC. Thirty-four (34) samples with altered gyrA could be grouped into twelve (12) distinct Neisseria gonorrhoeae genotypes. The most frequent Neisseria gonorrhoeae genotype observed was CIP-R1. The CIP-R1 genotype includes ins345A (penA), S91F (gyrA), D95G (gyrA), S87R (parC), L421P (ponA), G120K (porB), A121D (porB), -35delA (mtrR) and V57M (rpsJ) antibiotic resistance mutations. Such an abundance of antibiotic resistance mutations suggests that corresponding Neisseria gonorrhoeae isolates may exhibit multidrug resistance phenotypes to penicillin, ciprofloxacin, tetracycline, and azithromycin.

Currently, the alarming trend observed in sexually transmitted disease management is the emerging resistance to the oral cephalosporin cefixime in Neisseria gonorrhoeae. Mosaic changes in the penA gene, including the G545S substitution, are recognized genetic markers associated with loss of susceptibility to cefixime. We found mosaic penA genes bearing the G545S mutation in five (5) Neisseria gonorrhoeae-positive clinical samples. Three (3) of the five (5) Neisseria gonorrhoeae-positive clinical samples identified as having mosaic penA genes were of the CFM-R1 genotype. Two (2) of the five (5) Neisseria gonorrhoeae-positive clinical samples identified as having mosaic penA genes were of the CFM-R2 genotype. The CFM-R1 genotype includes G545S (mosaic penA), S91F (gyrA), D95G (gyrA), S87R (parC), L421P (ponA), G120K (porB), A121D (porB), -35delA (mtrR) and V57M (rpsJ) antibiotic resistance mutations. The CFM-R2 genotype includes G545S (mosaic penA), G45D (mtrR) and V57M (rpsJ) antibiotic resistance mutations. Interestingly, the CFM-R1 genotype is identical to the most frequent ciprofloxacin resistance genotype, CIP-R1, but for the addition of the G545S (mosaic penA) mutation found in CFM-R1. Our identification of the CFM-R1 genotype may indicate that these cefixime-resistant Neisseria gonorrhoeae isolates developed in the background of existing multidrug resistant strains.

Reduced susceptibility to a number of antimicrobial agents (e.g., oral cephalosporins, penicillins, fluoroquinolones, tetracyclines and macrolides) has been described for multidrug resistant Neisseria gonorrhoeae isolates in Japan. Our data suggest that such multidrug resistant Neisseria gonorrhoeae strains may already be prevalent among the general population in the continental United States.

Table 11 summarizes the genetic markers of antibiotic resistance in Neisseria gonorrhoeae identified by our assay using five hundred eighty-three (583) clinical cervicovaginal samples tested that were positively identified by qPCR.

TABLE 11

Genetic markers of antibiotic resistance in Neisseria gonorrhoeae identified by our assay using five hundred eighty-three (583) clinical cervicovaginal samples tested that were positively identified by qPCR

| Gene Mutation in # of Clinical Samples (%) | Mutation/Marker | Total number | % of Mutation/Marker |
|---|---|---|---|
| penA 480 (82%) | G545S (mosaic penA) | 5 | 1 |
|  | ins345A | 475 | 81 |
| gyrA 34 (6%) | S91F | 34 | 6 |
|  | S91P | 0 | 0 |
|  | S91Y | 0 | 0 |
|  | D95A | 6 | 1 |
|  | D95G | 28 | 5 |
|  | D95N | 0 | 0 |
|  | D95Y | 0 | 0 |
| parC 33 (6%) | D86N | 1 | 0 |
|  | S87R | 28 | 5 |
|  | S87N | 4 | 1 |
|  | S88P | 0 | 0 |
|  | E91G | 1 | 0 |
|  | E91K | 0 | 0 |
| ponA 162 (28%) | L421P | 162 | 28 |
| porB (penB) 220 (38%) | G120K | 48 | 8 |
|  | G120D | 36 | 6 |
|  | A121D | 76 | 13 |
|  | A121S | 131 | 22 |
|  | A121G | 3 | 1 |
| mtrR 186 (32%) | -35delA | 64 | 11 |
|  | G45D | 114 | 20 |
|  | G45S | 0 | 0 |
|  | -10insTT | 33 | 6 |
| rpsJ 313 (54%) | V57M | 313 | 54 |
| 16s rRNA 2 (0%) | G1064C | 1 | 0 |
|  | C1192U | 1 | 0 |
| Plasmid 7 (1%) | bla | 7 | 1 |
| Plasmid 24 (4%) | tetM | 24 | 4 |

Example 11

Frequency of Antibiotic Resistance Mutations in Neisseria gonorrhoeae from One Thousand Three Hundred Twelve (1,312) Clinical Samples We have further expanded our clinical study. In this expanded study, we included and analyzed a total of one thousand three hundred twelve (1,312) clinical cervicovaginal samples previously diagnosed positive for Neisseria gonorrhoeae by qPCR. Note that the expanded study data is a combination of the data presented in Example 10 (above) and an addition of 692 clinical samples.

Using the panel assay listed in Table 1 (above), one thousand two hundred forty six (1,246) out of one thousand three hundred twelve (1,312) Neisseria gonorrhoeae samples produced reliable readouts with 95% concordance to the qPCR results. One thousand one hundred fifty (1,150) out of the one thousand two hundred forty six (1,246) Neisseria gonorrhoea-positive samples (92%) had at least one chromosomal antibiotic resistance mutation.

It is noted that the most frequent genetic changes identified were gene rearrangements in penA (1,053 of the 1,246 samples), which are predictive of resistance to penicillin, as well as a mutation in rpsJ (667 of the 1246 samples), which confers resistance to tetracycline. Cefixime, ciprofloxacin, penicillin, tetracycline and azithromycin resistance mutations in genes penA (7 of the 1,246 samples), mtrR (399 of the 1,246 samples), penB (440 of the 1,246 samples), ponA (355 of the 1,246 samples), gyrA (73 of the 1,246 samples), parC (72 of the 1,246 samples) and 16s rRNA (2 of the 1,246 samples) were also detected. In addition, plasmid-born bla genes (14 of the 1,246 samples) and plasmid-born tetM genes (58 of the 1,246 samples) were identified.

Because ciprofloxacin was the drug of choice for gonorrhea treatment until 2006, and cephalosporins are currently recommended for the same purpose by the CDC, we further analyzed the distribution of ciprofloxacin and cefixime (i.e., cephalosporin) mutations.

In all the samples harboring gyrA mutations conferring resistance to ciprofloxacin (73 samples), the S91F mutation was linked with either the D95G (61 samples) or the D95A (12 samples) mutation. There was a strong association between gyrA mutations and mutations in rpsJ (V57M), penA (Asp345a), and ponA (L421P). In all cases, gyrA ciprofloxacin resistance mutations were accompanied by either the D86N (1 sample), S87N (9 samples), S87R (61 samples), E91K (1 sample), or E91G (1 sample) mutation in parC. Seventy-three (73) samples with altered gyrA could be grouped into fifteen (15) distinct *N. gonorrhoeae* genotypes. The most frequent *Neisseria gonorrhoeae* genotype observed was CIP-R1. The CIP-R1 genotype (30 samples) includes Asp345a (penA), S91F (gyrA), D95G (gyrA), S87R (parC), L421P (ponA), G120K (porB), A121D (porB), −35delA (mtrR) and V57M (rpsJ) antibiotic resistance mutations. The abundance of antibiotic resistance mutations suggests that corresponding *Neisseria gonorrhoeae* isolates may exhibit multidrug resistance phenotypes to penicillin, ciprofloxacin, tetracycline, and azithromycin.

Currently, the alarming trend observed in sexually transmitted disease management is the emerging resistance to the oral cephalosporin cefixime in *Neisseria gonorrhoeae*. Mosaic changes in the penA gene, including the G545S substitution, are recognized genetic markers associated with loss of susceptibility to cefixime. We found mosaic penA genes bearing the G545S mutation in seven (7) *Neisseria gonorrhoeae*-positive clinical samples. Two (2) of the seven (7) *Neisseria gonorrhoeae*-positive clinical samples identified as having mosaic penA genes were of the CFM-R1 genotype. Three (3) of the seven (7) *Neisseria gonorrhoeae*-positive clinical samples identified as having mosaic penA genes were of the CFM-R2 genotype. The CFM-R2 genotype includes G545S (mosaic penA), S91F (gyrA), D95G (gyrA), S87R (parC), L421P (ponA), G120K (porB), A121D (porB), −35delA (mtrR) and V57M (rpsJ) antibiotic resistance mutations. Two (2) of the seven (7) *Neisseria gonorrhoeae*-positive clinical samples identified as having mosaic penA genes were of the CFM-R3 genotype. The CFM-R3 genotype includes G545S (mosaic penA), G45D (mtrR) and V57M (rpsJ) antibiotic resistance mutations. Interestingly, the CFM-R1 genotype is identical to the most frequent ciprofloxacin resistance genotype, CIP-R1, but for the addition of the G545S (mosaic penA) mutation found in CFM-R1. Our identification of the CFM-R1 genotype may indicate that these cefixime-resistant *Neisseria gonorrhoeae* isolates developed in the background of existing multidrug resistant strains.

Reduced susceptibility to a number of antimicrobial agents (e.g., oral cephalosporins, penicillins, fluoroquinolones, tetracyclines and macrolides) has been described for multidrug resistant *Neisseria gonorrhoeae* isolates in Japan. Our data suggest that such multidrug resistant *Neisseria gonorrhoeae* strains may already be prevalent among the general population in the continental United States.

Table 12 summarizes the genetic markers of antibiotic resistance in *Neisseria gonorrhoeae* identified by our assay using one thousand two hundred forty six (1,246) clinical cervicovaginal samples tested that were positively identified by qPCR.

TABLE 12

Genetic markers of antibiotic resistance in *Neisseria gonorrhoeae* identified by our assay using one thousand two hundred forty six (1,246) clinical cervicovaginal samples tested that were positively identified by qPCR

| Gene Mutation in # of Clinical Samples (%) | Mutation/Marker | Total number | % of Mutation/Marker |
|---|---|---|---|
| penA 1053 (85%) | G545S (mosaic penA) | 7 | 1 |
|  | ins345A | 1046 | 84 |
| gyrA 73 (6%) | S91F | 73 | 6 |
|  | S91P | 0 | 0 |
|  | S91Y | 0 | 0 |
|  | D95A | 12 | 1 |
|  | D95G | 61 | 5 |
|  | D95N | 0 | 0 |
|  | D95Y | 0 | 0 |
| parC 72 (6%) | D86N | 1 | 0 |
|  | S87R | 61 | 5 |
|  | S87N | 9 | 1 |
|  | S88P | 0 | 0 |
|  | E91G | 1 | 0 |
|  | E91K | 1 | 0 |
| ponA 355 (28%) | L421P | 355 | 28 |
| porB (penB) 440 (35%) | G120K | 101 | 8 |
|  | G120D | 69 | 6 |
|  | A121D | 150 | 12 |
|  | A121S | 262 | 21 |
|  | A121G | 16 | 1 |
| mtrR 399 (32%) | −35delA | 138 | 11 |
|  | G45D | 265 | 21 |
|  | G45S | 0 | 0 |
|  | −10insTT | 52 | 4 |
| rpsJ 667 (54%) | V57M | 667 | 54 |
| 16s rRNA 2 (0%) | G1064C | 1 | 0 |
|  | C1192U | 1 | 0 |
| Plasmid 7 (1%) | bla | 14 | 1 |
| Plasmid 24 (4%) | tetM | 58 | 5 |

EXPERIMENTAL REAGENTS AND PROTOCOLS

A) Multiplex PCR for *Neisseria gonorrhoeae*

Eight-(8) tube strip was used. Four (4) pre-mixed PCR reactions (i.e., 1, 2, 3, and 4) are used for processing of individual DNA sample. Reactions are pre-mixed and placed in the 8-tube strip. Each PCR reaction requires 5 µl from total DNA sample.

The genes amplified and the respective mutation/genetic markers are listed as followed:

| PCR | Genes Amplified | Mutation/Marker |
|---|---|---|
| 1 | penA, ponA, penB | Normal(penA), Mosaic(penA), G545S(penA), L421(ponA), L421P(ponA), G120(porB), G120K(porB), G120D(porB), A121(porB), A121D(porB), A121S(porB), A121G(porB) |
| 2 | porA, penA, rpsJ | N. gon(porA), Asp345(penA), Asp345A(penA), V57(rpsJ), V57M(rpsJ) |
| 3 | gyrA, parC, 16s rRNA | S91(gyrA), S91F(gyrA), S91P(gyrA), S91Y(gyrA), D95(gyrA), D95A(gyrA), D95G(gyrA), D95N(gyrA), D95Y(gyrA), D86N(parC), S87(parC), S87R(parC), S87N(parC), S88P(parC), E91(parC), E91K(parC), E91G(parC), G1064(16s rRNA), G1064C(16s rRNA), C1192(16s rRNA), C1192U(16s rRNA) |
| 4 | mtrR, bla, tet(M) | −35delA(mtrR), −35delA(mtrR), G45(mtrR), G45D(mtrR), G45S(mtrR), −10insTT(mtrR), −10insTT(mtrR) |

The multiplex PCR procedures involve opening 8-tube strip containing 4 individual 20-μl pre-mixed PCR mixes (1, 2, 3, and 4). And the contents in the 8-cap strip are then discarded. An aliquots of 5 μl from total DNA sample are added into 4 PCR mixes in the 8-tube strip (1, 2, 3, and 4) and sealed with new 8-cap strip. The contents are mixed thoroughly and spin down on microcentrifuge. The 8-cap strip is then loaded into a thermocycler. Total number of amplification cycles is 35. After run completion PCR reaction can be kept at 4° C. if used during the day or frozen at −20° C. for longer storage.

The PCR program conditions include an initial denaturation (95° C., 3 minutes), cycling (35 cycles): 95° C., 30 seconds, 55° C., 30 seconds, 72° C., 30 seconds. Final elongation includes 72° C., 3 minutes.

B) Exo-SAP IT Treatment of PCRs

This step is optional. After the multiplex PCR, open the 8-tube strip containing the 4 PCRs (1, 2, 3, and 4) and discard the 8-cap strip. Take aliquots of 2 μl from each of multiplex PCRs (1, 2, 3, and 4) and pipette them into new 200 μl PCR tube. Then add 3.2 μl of ExoSAP-IT® (USB) and mix thoroughly, followed by microcentrifuging.

Load PCR tube into a thermocycler. Start the PCR run. After run completion EXO-SAP IT reaction can be kept at 4° C. if used during the day or frozen at −20° C. for longer storage.

The PCR program conditions include the following steps: (i) primers and nucleotide clean-up (37° C., 15 minutes) (function to clean up primers and nucleotides); (ii) ExoSAP-IT deactivation (80° C., 15 minutes) (function to ExoSAP-IT deactivation); and (iii) pause (4° C., hold) (function to hold the reaction).

C) Multiplex Allele-Specific Primer Extension (ASPE) Reaction

Into a 200-μl PCR tube containing a pre-mixed *Neisseria gonorrhoeae* ASPE mix, add aliquot of 5 μl of ExoSAP-IT® treated PCR, and mix the content thoroughly, followed by micro centrifuging.

Load PCR tube with ASPE reaction into a thermocycler. Start run PCR program. Total number of amplification cycles is 35, and total time is 1 hour 57 minutes. After completion of the ASPE reaction, the tube can be kept at 4° C. if used during the day or frozen at −20° C. for longer storage.

D) Multiplex FlexMAP Hybridization

Prepare Hybridization Mastermix by mixing 30 μl of *Neisseria gonorrhoeae* FlexMAP Mastermix (mix thoroughly before taking an aliquot) and 35 μl of 2×NaCl Hybridization buffer. Mix thoroughly. Do not centrifuge.

Add aliquot of 5 μl of into tube containing Hybridization Mastermix. Mix thoroughly and do not centrifuge. Load tube into a Thermocycler. Start PCR run. Total time is 20 minutes. After hybridization proceed immediately to filtering and SAPE labeling.

The FLEX program conditions includes three (3) steps: (i) denaturation (95° C., 3 minutes) (function to denature); (ii) FlexMAP hybridization step (37° C., 15 minutes) (function to FlexMAP hybridization); (iii) pause (37° C., hold) (function to hold reaction).

E) Filtering and SAPE Labeling

Transfer hybridization reaction from PCR tube to a Millipore filter plate. Vacuum the filter plate (Blot on a paper towel). Add 75 μl of 1×NaCl hybridization buffer and vacuum filter plate. (Blot on a paper towel). Add 75 μl of SAPE buffer. Shake the plate on orbital shaker at 300 rpm for 10 minutes. Vacuum the filter plate (Blot on a paper towel). Add 75 μl of 1×NaCl hybridization buffer. Shake the plate on orbital shaker at 300 rpm for 10 minutes. Transfer the entire volume (75 μl) of reaction from Millipire filter plate to 96 well Polycarbonate Costar plate.

F) Bio-Plex Run

Turn on the Array Reader, Microplate Platform and Fluidics Pump. Load MCV plate filled with water and isopropanol. Load MCV plate filled with water and calibrators. Calibrate the system. Create *Neisseria gonorrhoeae* Panel protocol file. Select analytes set by choosing *Neisseria gonorrhoeae* Panel profile. Format plate, and enter sample information. Set the temperature of 37° C. using Platform Heater. Load 96-well Costar plate with labeling reactions. Start run. After run completion, unload and discard the plate. Load MCV plate filled with water and 10% bleach.

The foregoing detailed description provides exemplary embodiments of the invention and includes the best mode for practicing the invention. The description and illustration of embodiments is intended only to provide examples of the invention and not to limit the scope of the invention, or its protection, in any manner. All patents, patent applications, publications and other materials cited herein are hereby incorporated by reference in their entirety.

REFERENCES

1. Derrick, Jeremy P. et al. Structural and Evolutionary Inference from Molecular Variation in *Neisseria* Porins. Infection and Immunity 1999; 67(5): 2406-2413.
2. Hjelmevoll, Stig Ove et al. A Fast Real-Time Polymerase Chain Reaction Method for Sensitive and Specific Detection of *Neisseria gonorrhoeae* porA Pseudogene. Journal of Molecular Diagnostics 2006; 8(5): 574-581.
3. Hjelmevoll, Stig Ove et al. Clinical Validation of a Real-Time Polymerase Chain Reaction Detection of *Neisseria gonorrhoeae* porA Pseudogene Versus Culture Techniques. Sexually Transmitted Diseases 2008; 35(5): 517-520.
4. de Filippis, I. et al. *Neisseria meningitidis* PorA variable regions: rapid detection of P1-7 and P1-19 variants by PCR. Letters in Applied Microbiology 2007; 45: 426-431.
5. Goire, Namraj et al. A duplex *Neisseria gonorrhoeae* real-time polymerase chain reaction assay targeting the gonococcal porA pseudogene and multicopy opa genes. Diagnostic Microbiology and Infectious Disease 2008; 61: 6-12.
6. Ito, Masayasu et al. Emergence and Spread of *Neisseria gonorrhoeae* Clinical Isolates Harboring Mosaic-Like Structure of Penicillin-Binding Protein 2 in Central Japan. Antimicrobial Agents and Chemotherapy 2005; 49(1): 137-143.
7. Takahata, Sho et al. Amino Acid Substitutions in Mosaic Penicillin-Binding Protein 2 Associated with Reduced Susceptibility to Cefixime in Clinical Isolates of *Neisseria gonorrhoeae*. Antimicrobial Agents and Chemotherapy 2006; 50(11): 3638-3645.
8. Thulin, Sara et al. Combined Real-Time PCR and Pyrosequencing Strategy for Objective, Sensitive, Specific, and High-Throughput Identification of Reduced Susceptibility to Penicillins in *Neisseria meningitidis*. Antimicrobial Agents and Chemotherapy 2008; 52(2): 753-756.
9. Ochiai, Susumu et al. Rapid Detection of the Mosaic Structure of the *Neisseria gonorrhoeae* penA Gene, Which Is Associated with Decreased Susceptibilities to Oral Cephalosporins. Journal of Clinical Microbiology 2008; 46(5): 1804-1810.
10. Tanaka, Masatoshi et al. Analysis of mutations within multiple genes associated with resistance in a clinical isolate of *Neisseria gonorrhoeae* with reduced ceftriaxone susceptibility that shows a multidrug-resistant phenotype. International Journal of Antimicrobial Agents 2006; 27: 20-26.
11. Pnadori, Mark et al. Mosaic Penicillin-Binding Protein 2 in *Neisseria gonorrhoeae* Isolates Collected in 2008 in San Francisco, Calif. Antimicrobial Agents and Chemotherapy 2009; 53(9): 4032-4034.
12. Ohnishi, Makoto et al. Spread of a Chromosomal Cefixime-Resistant penA Gene among Different *Neisseria gonorrhoeae* Lineages. Antimicrobial Agents and Chemotherapy 2010; 54(3): 1060-1067.
13. Deguchi, Takashi et al. DNA Gyrase Mutations in Quinolone-Resistant Clinical Isolates of *Neissera gonorrhoeae*. Antimicrobial Agents and Chemotherapy 1995; 39(2): 561-563.
14. Deguchi, Takashi et al. Quinolone-Resistant *Neisseria gonorrhoeae*: Correlation of Alterations in the GyrA Subunit of DNA Gyrase and the ParC Subunit of Topoisomerase IV with Antimicrobial Susceptibility Profiles. Antimicrobial Agents and Chemotherapy 1996; 40(4): 1020-1023.
15. Trees, David L. et al. Alterations within the quinolone resistance-determining regions of GyrA and ParC of *Neissera gonorrhoeae* isolated in the Far East and the United States. International Journal of Antimicrobial Agents 1999; 12: 325-332.
16. Sultan, Zafar et al. Comparison of Mismatch Amplification Mutation Assay with DNA Sequencing for Characterization of Fluoroquinolone Resistance in *Neissera gonorrhoeae*. Journal of Clinical Microbiology 2004; 42(2): 591-594.
17. Vernel-Pauillac, Frederique et al. Quinolone Resistance in *Neissera gonorrhoeae*: Rapid Genotyping of Quinolone Resistance-Determining Regions in gyrA and parC Genes by Melting Curve Analysis Predicts Susceptibility. Antimicrobial Agents and Chemotherapy 2009; 53(3): 1264-1267.
18. Tanaka, Masatoshi et al. Analysis of quinolone resistance mechanisms in *Neissera gonorrhoeae* isolates in vitro. Sex Transm Inf 1998; 74: 59-62.
19. Shigemura, Katsumi et al. Rapid detection of the fluoroquinolone resistance-associated ParC mutation in *Neissera gonorrhoeae* using TaqMan probes. International Journal of Urology 2006; 13: 277-281.
20. Ropp, Patricia A. et al. Mutations in ponA, the Gene Encoding Penicillin-Binding Protein 1, and a Novel Locus, penC, Are Required for High-Level Chromosomally Mediated Penicillin Resistance in *Neissera gonorrhoeae*. Antimicrobial Agents and Chemotherapy 2002; 46(3): 769-777.
21. Shigemura, Katsumi et al. Presence of a mutation in ponA1 of *Neisseria gonorrhoeae* in numerous clinical samples resistant to various β-lactams and other, structurally unrelated, antimicrobials. Journal Infect Chemother 2005; 11: 226-230.
22. Kugelman, Gayle et al. Simple, Rapid, and Inexpensive Detection of *Neissera gonorrhoeae* Resistance Mechanisms Using Heat-Denatured Isolates and SYBR Green-Based Real-Time PCR. Antimicrobial Agents and Chemotherapy 2009; 53(10): 4211-4216.
23. Olesky, Melanie et al. Identification and Analysis of Amino Acid Mutations in Porin IB That Mediate Intermediate-Level Resistance to Penicillin and Tetracycline in *Neisseria gonorrhoeae*. Antimicrobial Agents and Chemotherapy 2002; 46(9): 2811-2820.
24. Olesky, Melanie et al. Porin-Mediated Antibiotic Resistance in *Neisseria gonorrhoeae*: Ion, Solute, and Antibiotic Permeation through PIB Proteins with penB Mutations. Journal of Bacteriology 2006; 188(7): 2300-2308.
25. Vernel-Pauillac, Frederique et al. Genotyping as a Tool for Antibiotic Resistance Surveillance of *Neissera gonorrhoeae* in New Caledonia: Evidence of a Novel Genotype Associated with Reduced Penicillin Susceptibility. Antimicrobial Agents and Chemotherapy 2008; 52(9): 3293-3300.
26. Zarantonelli, Leticia et al. Decreased Azithromycin Susceptibility of *Neisseria gonorrhoeae* Due to mtrR Mutations. Antimicrobial Agents and Chemotherapy 1999; 43(10): 2468-2472.
27. Dewi, Beti Ernawati et al. High Occurrence of Simultaneous Mutations in Target Enzymes and MtrRCDE Efflux System in Quinolone-Resistant *Neisseria gonorrhoeae*. Sexually Transmitted Diseases 2004; 31(6): 353-359.
28. Hu, Mei et al. High-Level Chromosomally Mediated Tetracycline Resistance in *Neisseria gonorrhoeae* Results from a Point Mutation in the rpsJ Gene Encoding Ribosomal Protein S10 in Combination with the mtrR and penB Resistance Determinants. Antimicrobial Agents and Chemotherapy 2005; 49(10): 4327-4334.
29. Ison, Catherine A. et al. Detection of the tetM Determinant in *Neisseria gonorrhoeae*. Sexually Transmitted Diseases 1993; 20(6): 329-333.
30. Turner, A. et al. Molecular Epoidemiology of tetM genes in *Neisseria gonorrhoeae*. Sex Transm Inf 1999; 75: 60-66.
31. Xia, Minsheng et al. Detection of two groups of 25-2 MDa Tet M plasmids by polymerase chain reaction of the downstream region. Molecular and Cellular Probes 1995; 9: 327-332.
32. Elwell, Lynn P. et al. Plasmid-Mediated Beta-Lactamase Production in *Neisseria gonorrhoeae*. Antimicrobial Agents and Chemotherapy 1977; 11(3): 528-533.
33. Dillon, J. R. et al. A PCR assay for discriminating *Neisseria gonorrhoeae* β-lactamase-producing plasmids. Molecular and Cellular Probes 1999; 13: 89-92.
34. Palmar, H. M. et al. A multiplex polymerase chain reaction to differentiate β-lactamase plasmids of *Neisseria gonorrhoeae*. Journal of Antimicrobial Chemotherapy 2000; 45: 777-782.
35. Galimand, Marc et al. Spectinomycin Resistance in *Neisseria* spp. Due to Mutations in 16S rRNA. Antimicrobial Agents and Chemotherapy 2000; 44(5): 1365-1366.

What is claimed is:

1. A method of generating an antibiotic resistance profile for *Neisseria gonorrhoeae* against penicillin, tetracycline, ceftriaxone, ciprofloxacin, spectinomycin and azithromycin in a human, comprising the steps of:

a) obtaining a biological sample from a human, said biological sample is a vaginal swab, uretheral swab, ocular swab or urine;

b) isolating DNA from said biological sample;

c) performing four multiplex PCR against a plurality of genes of penA, penB, ponA, porA, parC, rpsJ, gyrA, 16S rRNA, mtrR, bla and tet(M) in *Neisseria gonorrhoeae* to produce respective amplicons of said genes, said multiplex PCR comprising:

i. a first multiplex PCR containing a plurality of primer sets against penA, penB, and ponA, said plurality of primer sets consists of: (i) a forward primer (SEQ ID NO: 1) and a reverse primer (SEQ ID NO: 2) against penA, (ii) a forward primer (SEQ ID NO: 5) and a reverse primer (SEQ ID NO: 6) against penB, and (iii) a forward primer (SEQ ID NO: 3) and a reverse primer (SEQ ID NO: 4) against ponA;

ii. a second multiplex PCR containing a plurality of primer sets against porA, penA, and rpsJ, said plurality of primer sets consists of: (i) a forward primer (SEQ ID NO: 7) and a reverse primer (SEQ ID NO: 8) against porA, (ii) a forward primer (SEQ ID NO: 1) and a reverse primer (SEQ ID NO: 2) against penA, and (iii) a forward primer (SEQ ID NO: 11) and a reverse primer (SEQ ID NO: 12) against rspJ;

iii. a third multiplex PCR containing a plurality of primer sets against gyrA, parC, and 16S rRNA, said plurality of primer sets consists of: (i) a forward primer (SEQ ID NO: 13) and a reverse primer (SEQ ID NO: 14) against gyrA, (ii) a forward primer (SEQ ID NO: 15) and a reverse primer (SEQ ID NO: 16) against parC, and (iii) a forward primer (SEQ ID NO: 17) and a reverse primer (SEQ ID NO: 18) against 16S rRNA; and iv. a fourth multiplex PCR containing a plurality of primer sets against mtrR, bla, and tet(M), said plurality of primer sets consists of: (i) a forward primer (SEQ ID NO: 19) and a reverse primer (SEQ ID NO: 20) against mtrR, (ii) a forward primer (SEQ ID NO: 21) and a reverse primer (SEQ ID NO: 22) against bla, and (iii) a forward primer (SEQ ID NO: 23) and a reverse primer (SEQ ID NO: 24) against tet(M);

d) performing a multiplex allele-specific primer extension reaction on said respective amplicons in step (c) to produce an extended primer for said respective amplicons;

e) detecting the presence of said extended primers for said respective amplicons produced by:

(i) porA gene;

(ii) tet(M) gene;

(iii) bla gene; and (iv) penA, penB, ponA, parC, rpsJ, gyrA, 16S rRNA, and mtrR genes; and f) determining that said presence of said extended primer for said amplicon produced by porA gene is indicative of the presence of *Neisseria gonorrhoeae*, said presence of said extended primer for said amplicon produced by tet(M) gene is indicative of tetracycline resistance in *Neisseria gonorrhoeae*, said presence of said extended primer for said amplicon produced by bla gene is indicative of penicillin resistance in *Neisseria gonorrhoeae*, and said presence of said extended primers for amplicons produced by penA, penB, ponA, parC, rpsJ, gyrA, 16S rRNA, and mtrR genes are indicative of the presence of a mutation in said genes in *Neisseria gonorrhoeae*, and said presence of said mutation in penA, penB, ponA, parC, rpsJ, gyrA, 16S rRNA, and mtrR permits the generation of an antibiotic resistance profile against penicillin, tetracycline, ceftriaxone, ciprofloxacin, spectinomycin, and azithromycin in *Neisseria gonorrhoeae*, and wherein said method has an analytical sensitivity of 25 femtograms of *Neisseria gonorrhoeae* chromosomal DNA, and said method is useful in selecting antibiotic to treat gonorrhea infection in said human, based on said antibiotic resistance profile.

2. The method of claim 1, wherein said isolating step is performed using guanidine hydrochloride, guanidine thiocyanate, or phenol chloroform.

3. The method of claim 1, wherein said mutation in penA is selected from the group consisting of G545S, and Asp345A.

4. The method of claim 1, wherein said mutation in penB is selected from the group consisting of G120D, G120K, A121D, A121S, and A121G.

5. The method of claim 1, wherein said mutation in rpsJ is V57M.

6. The method of claim 1, wherein said mutation in gyrA is selected from the group consisting of S91P, S91F, S91Y, D95A, D95G, D95N, and D95Y.

7. The method of claim 1, wherein said mutation in 16S rRNA is selected from the group consisting of G1064C and C1192U.

8. The method of claim 1, wherein said mutation in mtrR is selected from the group consisting of G45D, G45S, −35delA, and −10insTT.

9. The method of claim 1, wherein said mutation in ponA is L421P.

10. The method of claim 1, wherein said mutation in parC is selected from the group consisting of D86N, S87R, S87N, S88P, E91K, and E91G.

11. The method claim 1, wherein said bla gene plasmid is selected from the group consisting of pSJ5, pJD4, pAB6, and pFA7.

12. The method of claim 4, wherein said tetM gene plasmid is pOZ100.

* * * * *

SEQUENCE LISTING

<160> NUMBER OF SEQ ID NOS: 55

<210> SEQ ID NO 1
<211> LENGTH: 22
<212> TYPE: DNA
<213> ORGANISM: Neisseria gonorrhoeae

<400> SEQUENCE: 1
ccgtgtgatt gtggcggtaa cc                                              22

<210> SEQ ID NO 2
<211> LENGTH: 21
<212> TYPE: DNA
<213> ORGANISM: Neisseria gonorrhoeae

<400> SEQUENCE: 2
tgcccaagat gttcaggctg c                                               21

<210> SEQ ID NO 3
<211> LENGTH: 24
<212> TYPE: DNA
<213> ORGANISM: Neisseria gonorrhoeae

<400> SEQUENCE: 3
gagcggtcga taatgagaaa atgg                                            24

<210> SEQ ID NO 4
<211> LENGTH: 20
<212> TYPE: DNA
<213> ORGANISM: Neisseria gonorrhoeae

<400> SEQUENCE: 4
gcatccagcg aaaccaaagc                                                 20

<210> SEQ ID NO 5
<211> LENGTH: 25
<212> TYPE: DNA
<213> ORGANISM: Neisseria gonorrhoeae

<400> SEQUENCE: 5
caacaaacaa tccttcgtcg gcttg                                           25

<210> SEQ ID NO 6
<211> LENGTH: 24
<212> TYPE: DNA
<213> ORGANISM: Neisseria gonorrhoeae

<400> SEQUENCE: 6
ggcaaattcg ggagaatcgt agcg                                            24

<210> SEQ ID NO 7
<211> LENGTH: 20
<212> TYPE: DNA
<213> ORGANISM: Neisseria gonorrhoeae

<400> SEQUENCE: 7
ccgtgcgtta cgattccccc                                                 20

<210> SEQ ID NO 8
<211> LENGTH: 23
<212> TYPE: DNA
<213> ORGANISM: Neisseria gonorrhoeae

<400> SEQUENCE: 8

-continued

```
acagccggaa ctggtttcat ctg                                           23

<210> SEQ ID NO 9
<211> LENGTH: 22
<212> TYPE: DNA
<213> ORGANISM: Neisseria gonorrhoeae

<400> SEQUENCE: 9
ttcggcaatc aaaccgttcg tg                                            22

<210> SEQ ID NO 10
<211> LENGTH: 20
<212> TYPE: DNA
<213> ORGANISM: Neisseria gonorrhoeae

<400> SEQUENCE: 10
tgcttgtgcc gacgttggac                                               20

<210> SEQ ID NO 11
<211> LENGTH: 24
<212> TYPE: DNA
<213> ORGANISM: Neisseria gonorrhoeae

<400> SEQUENCE: 11
gcgtttcaac attttgcgtt ctcc                                          24

<210> SEQ ID NO 12
<211> LENGTH: 26
<212> TYPE: DNA
<213> ORGANISM: Neisseria gonorrhoeae

<400> SEQUENCE: 12
catcggtagt tttatcggtc caatcc                                        26

<210> SEQ ID NO 13
<211> LENGTH: 23
<212> TYPE: DNA
<213> ORGANISM: Neisseria gonorrhoeae

<400> SEQUENCE: 13
aaaataactg gaatgccgcc tac                                           23

<210> SEQ ID NO 14
<211> LENGTH: 22
<212> TYPE: DNA
<213> ORGANISM: Neisseria gonorrhoeae

<400> SEQUENCE: 14
gaagttgccc tgtccgtcta tc                                            22

<210> SEQ ID NO 15
<211> LENGTH: 20
<212> TYPE: DNA
<213> ORGANISM: Neisseria gonorrhoeae

<400> SEQUENCE: 15
cgtggtcggc gagattttgg                                               20

<210> SEQ ID NO 16
<211> LENGTH: 20
<212> TYPE: DNA
<213> ORGANISM: Neisseria gonorrhoeae
```

<400> SEQUENCE: 16
cgaaccgaag ttgccgatgc                                          20

<210> SEQ ID NO 17
<211> LENGTH: 20
<212> TYPE: DNA
<213> ORGANISM: Neisseria gonorrhoeae

<400> SEQUENCE: 17
agccgtaaca caggtgctgc                                          20

<210> SEQ ID NO 18
<211> LENGTH: 24
<212> TYPE: DNA
<213> ORGANISM: Neisseria gonorrhoeae

<400> SEQUENCE: 18
gaccattgta tgacgtgtga agcc                                     24

<210> SEQ ID NO 19
<211> LENGTH: 26
<212> TYPE: DNA
<213> ORGANISM: Neisseria gonorrhoeae

<400> SEQUENCE: 19
gggtttcatt atacatacac gattgc                                   26

<210> SEQ ID NO 20
<211> LENGTH: 22
<212> TYPE: DNA
<213> ORGANISM: Neisseria gonorrhoeae

<400> SEQUENCE: 20
gatgtcgtcg cagatacgtt gg                                       22

<210> SEQ ID NO 21
<211> LENGTH: 25
<212> TYPE: DNA
<213> ORGANISM: Neisseria gonorrhoeae

<400> SEQUENCE: 21
atagacagat cgctgagata ggtgc                                    25

<210> SEQ ID NO 22
<211> LENGTH: 23
<212> TYPE: DNA
<213> ORGANISM: Neisseria gonorrhoeae

<400> SEQUENCE: 22
aaaagcggtt agagcggcta ttg                                      23

<210> SEQ ID NO 23
<211> LENGTH: 23
<212> TYPE: DNA
<213> ORGANISM: Neisseria gonorrhoeae

<400> SEQUENCE: 23
ccagccccgt cgtccaaata gtc                                      23

<210> SEQ ID NO 24
<211> LENGTH: 24
<212> TYPE: DNA
<213> ORGANISM: Neisseria gonorrhoeae

```
<400> SEQUENCE: 24
gcatcaatca tttgctcatg tggc                                         24

<210> SEQ ID NO 25
<211> LENGTH: 48
<212> TYPE: DNA
<213> ORGANISM: Neisseria gonorrhoeae

<400> SEQUENCE: 25
cttttcaatt acttcaaatc ttcaaagagg ggtaaacatg ggtatcgt               48

<210> SEQ ID NO 26
<211> LENGTH: 48
<212> TYPE: DNA
<213> ORGANISM: Neisseria gonorrhoeae

<400> SEQUENCE: 26
tcattcatat acataccaat tcataagagg ggtaaacatg ggtatcgc               48

<210> SEQ ID NO 27
<211> LENGTH: 45
<212> TYPE: DNA
<213> ORGANISM: Neisseria gonorrhoeae

<400> SEQUENCE: 27
tcaacaatct tttacaatca aatcggtggt tcaagagccg ttgcc                  45

<210> SEQ ID NO 28
<211> LENGTH: 45
<212> TYPE: DNA
<213> ORGANISM: Neisseria gonorrhoeae

<400> SEQUENCE: 28
attattcact tcaaactaat ctaccagccc cctgaaaaac accga                  45

<210> SEQ ID NO 29
<211> LENGTH: 44
<212> TYPE: DNA
<213> ORGANISM: Neisseria gonorrhoeae

<400> SEQUENCE: 29
tacattacca ataatcttca atccagccc cctgaaaaac acca                    44

<210> SEQ ID NO 30
<211> LENGTH: 47
<212> TYPE: DNA
<213> ORGANISM: Neisseria gonorrhoeae

<400> SEQUENCE: 30
ctacatattc aaattactac ttacggattc ccaagcattg acgttgt                47

<210> SEQ ID NO 31
<211> LENGTH: 48
<212> TYPE: DNA
<213> ORGANISM: Neisseria gonorrhoeae

<400> SEQUENCE: 31
aatctaacaa actcatctaa atacggattc ccaagcattg acgttgct              48

<210> SEQ ID NO 32
<211> LENGTH: 48
<212> TYPE: DNA
```

<213> ORGANISM: Neisseria gonorrhoeae

<400> SEQUENCE: 32
ctatcttcat atttcactat aaacggattc ccaagcattg acgttgcc                 48

<210> SEQ ID NO 33
<211> LENGTH: 47
<212> TYPE: DNA
<213> ORGANISM: Neisseria gonorrhoeae

<400> SEQUENCE: 33
tcaactaact aatcatctat caattttgaa atgccaatag agcgcgt                  47

<210> SEQ ID NO 34
<211> LENGTH: 48
<212> TYPE: DNA
<213> ORGANISM: Neisseria gonorrhoeae

<400> SEQUENCE: 34
aatcaatctt cattcaaatc atcatttgaa atgccaatag agcgcgct                 48

<210> SEQ ID NO 35
<211> LENGTH: 53
<212> TYPE: DNA
<213> ORGANISM: Neisseria gonorrhoeae

<400> SEQUENCE: 35
taatcttcta tatcaacatc ttacttatac atacacgatt gcacggataa aaa           53

<210> SEQ ID NO 36
<211> LENGTH: 52
<212> TYPE: DNA
<213> ORGANISM: Neisseria gonorrhoeae

<400> SEQUENCE: 36
cttttacaat acttcaatac aatcggtttg acgagggcgg attataaaaa ag            52

<210> SEQ ID NO 37
<211> LENGTH: 52
<212> TYPE: DNA
<213> ORGANISM: Neisseria gonorrhoeae

<400> SEQUENCE: 37
tcataatctc aacaatcttt ctttgctgag ataggtgcct cactgattaa gc            52

<210> SEQ ID NO 38
<211> LENGTH: 48
<212> TYPE: DNA
<213> ORGANISM: Neisseria gonorrhoeae

<400> SEQUENCE: 38
tcatttacca atctttcttt ataccccgtc gtccaaatag tcggatag                 48

<210> SEQ ID NO 39
<211> LENGTH: 46
<212> TYPE: DNA
<213> ORGANISM: Neisseria gonorrhoeae

<400> SEQUENCE: 39
caatatcatc atctttatca ttacaacatt ttgcgttctc cgcaca                   46

<210> SEQ ID NO 40
<211> LENGTH: 44

```
<212> TYPE: DNA
<213> ORGANISM: Neisseria gonorrhoeae

<400> SEQUENCE: 40
tcatttcaca attcaattac tcaataccac ccccacggcg atcc            44

<210> SEQ ID NO 41
<211> LENGTH: 44
<212> TYPE: DNA
<213> ORGANISM: Neisseria gonorrhoeae

<400> SEQUENCE: 41
tcaatcaatt acttactcaa ataccgccat acggacgatg gtgg            44

<210> SEQ ID NO 42
<211> LENGTH: 45
<212> TYPE: DNA
<213> ORGANISM: Neisseria gonorrhoeae

<400> SEQUENCE: 42
cttttcaaat caatactcaa ctttcgccat acggacgatg gtgcc           45

<210> SEQ ID NO 43
<211> LENGTH: 45
<212> TYPE: DNA
<213> ORGANISM: Neisseria gonorrhoeae

<400> SEQUENCE: 43
ctttctacat tattcacaac attacgccat acggacgatg gtgtt           45

<210> SEQ ID NO 44
<211> LENGTH: 44
<212> TYPE: DNA
<213> ORGANISM: Neisseria gonorrhoeae

<400> SEQUENCE: 44
ttactacaca atatactcat caattaccac ccccacggcg atta            44

<210> SEQ ID NO 45
<211> LENGTH: 44
<212> TYPE: DNA
<213> ORGANISM: Neisseria gonorrhoeae

<400> SEQUENCE: 45
tcaatcatta cacttttcaa caattaccac ccccacggcg attt            44

<210> SEQ ID NO 46
<211> LENGTH: 44
<212> TYPE: DNA
<213> ORGANISM: Neisseria gonorrhoeae

<400> SEQUENCE: 46
caattcattt cattcacaat caatgccata cggacgatgg tgta            44

<210> SEQ ID NO 47
<211> LENGTH: 45
<212> TYPE: DNA
<213> ORGANISM: Neisseria gonorrhoeae

<400> SEQUENCE: 47
ataccaataa tccaattcat atcagtaaat accatccgca cggca           45

<210> SEQ ID NO 48
```

```
<211> LENGTH: 43
<212> TYPE: DNA
<213> ORGANISM: Neisseria gonorrhoeae

<400> SEQUENCE: 48
tacaaatcat caatcacttt aatctaccat ccgcacggcg acc                    43

<210> SEQ ID NO 49
<211> LENGTH: 43
<212> TYPE: DNA
<213> ORGANISM: Neisseria gonorrhoeae

<400> SEQUENCE: 49
caatttcatc attcattcat ttcaaccatc cgcacggcga caa                    43

<210> SEQ ID NO 50
<211> LENGTH: 43
<212> TYPE: DNA
<213> ORGANISM: Neisseria gonorrhoeae

<400> SEQUENCE: 50
caataaacta tacttcttca ctaacatccg cacggcgaca gtc                    43

<210> SEQ ID NO 51
<211> LENGTH: 43
<212> TYPE: DNA
<213> ORGANISM: Neisseria gonorrhoeae

<400> SEQUENCE: 51
ttcacttttc aatcaacttt aatcccatgc gcaccatcgc ctt                    43

<210> SEQ ID NO 52
<211> LENGTH: 42
<212> TYPE: DNA
<213> ORGANISM: Neisseria gonorrhoeae

<400> SEQUENCE: 52
ctttcaatta caatactcat tacaccatgc gcaccatcgc cc                     42

<210> SEQ ID NO 53
<211> LENGTH: 47
<212> TYPE: DNA
<213> ORGANISM: Neisseria gonorrhoeae

<400> SEQUENCE: 53
ttcaatcatt caaatctcaa ctttgccgac tgcaaacggt tactaca                47

<210> SEQ ID NO 54
<211> LENGTH: 47
<212> TYPE: DNA
<213> ORGANISM: Neisseria gonorrhoeae

<400> SEQUENCE: 54
ttactcaaaa tctacacttt ttcaaacatc tcacgacacg agctgag                47

<210> SEQ ID NO 55
<211> LENGTH: 47
<212> TYPE: DNA
<213> ORGANISM: Neisseria gonorrhoeae

<400> SEQUENCE: 55
cttttcatct tttcatcttt caatataagg gccatgagga cttgacg                47
```